(12) United States Patent
Udrea et al.

(10) Patent No.: US 10,488,358 B2
(45) Date of Patent: Nov. 26, 2019

(54) MICRO-HOTPLATE DEVICES WITH RING STRUCTURES

(71) Applicant: AMS Sensors UK Limited, Cambridge, Cambridgeshire (GB)

(72) Inventors: Florin Udrea, Cambridge (GB); Syed Zeeshan Ali, Cambridge (GB); Mohamed Foysol Chowdhury, Milton (GB)

(73) Assignee: AMS SENSORS UK LIMITED, Cambridge, Cambridgeshire (GB)

( * ) Notice: Subject to any disclaimer, the term of this patent is extended or adjusted under 35 U.S.C. 154(b) by 553 days.

(21) Appl. No.: 15/168,464

(22) Filed: May 31, 2016

(65) Prior Publication Data

US 2017/0343500 A1    Nov. 30, 2017

(51) Int. Cl.
*G01N 27/12* (2006.01)
*G01K 7/16* (2006.01)
(Continued)

(52) U.S. Cl.
CPC ............ *G01N 27/123* (2013.01); *G01K 7/16* (2013.01); *G01K 17/00* (2013.01); *G01N 27/128* (2013.01); *H01L 21/67109* (2013.01); *H05B 3/283* (2013.01); *G01N 27/16* (2013.01); *H05B 2203/017* (2013.01)

(58) Field of Classification Search
CPC .... G01N 27/123; G01N 27/128; G01N 27/16; G01K 7/16; G01K 17/00; H01L 21/67109; H01L 21/67103; H05B 2203/017; H05B 3/283
See application file for complete search history.

(56) References Cited

U.S. PATENT DOCUMENTS 4,580,439 A  *  4/1986  Manaka ................. G01N 27/12
                                                                    338/34
5,464,966 A     11/1995  Gaitan et al.
(Continued)

FOREIGN PATENT DOCUMENTS

DE    10315190 A1    10/2004
GB     2523788    *    9/2015
(Continued)

OTHER PUBLICATIONS

International Search Report and Written Opinion dated Dec. 13, 2017 for corresponding International application No. PCT/GB2017/051468.
(Continued)

*Primary Examiner* — Shawntina T Fuqua
(74) *Attorney, Agent, or Firm* — Tarolli, Sundheim, Covell & Tummino LLP

(57) ABSTRACT

We disclose a micro-hotplate comprising a substrate comprising an etched portion and a substrate portion and a dielectric region over the substrate. The dielectric region comprises first and second portions. The first portion is adjacent to the etched portion of the substrate and the second portion is adjacent to the substrate portion of the substrate. The micro-hotplate further comprises a heater formed in the dielectric region, and a ring structure formed within and/or over the dielectric region such that the ring structure is coupled with the first and second portions of the dielectric region.

32 Claims, 20 Drawing Sheets

(51) Int. Cl.
  *G01K 17/00* (2006.01)
  *H01L 21/67* (2006.01)
  *H05B 3/28* (2006.01)
  *G01N 27/16* (2006.01)

(56) References Cited

U.S. PATENT DOCUMENTS 8,552,380 B1 * 10/2013 Florin .................. G01J 5/12
                                                   250/338.4
2010/0147070 A1 * 6/2010 Jun ...................... G01N 27/121
                                                   73/335.05
2014/0105790 A1   4/2014 Gaudon et al.

FOREIGN PATENT DOCUMENTS

GB    2523788 A    9/2015
JP    2003294671 A    10/2003

OTHER PUBLICATIONS

Bhattacharyya, "Technological Journey Towards Reliable Microheater Development for MEMS Gas Sensors: A Review" IEEE Transactions on Device and Materials Reliability, vol. 14, No. 2, Jun. 2014, pp. 589-599.

Suehle, et al., "Tin Oxide Gas Sensor Fabricated Using CMOS Micro-Hotplates and In-Situ Processing" IEEE Electron Device Letters, vol. 14, No. 3, Mar. 1993, pp. 118-120.

Udrea, et al., "Design and Simulations of SOI CMOS Micro-Hotplate Gas Sensors" Sensors and Actuators B 78, 2001, pp. 180-190.

Afridi et al., "A Monolithic CMOS Microhotplate-Based Gas Sensor System" IEEE Sensors Journal, vol. 2, No. 6, Dec. 2002, pp. 644-655.

Graf et al., "CMOS Microhotplate Sensor System for Operating Temperatures up to 500oC" Sensors and Actuators B xxx (2005) 7 pages.

Ali, et al., "Tungsten-Based SOI Microhotplates for Smart Gas Sensors" Journal of Microelectromechanical Systems, vol. 17, No. 6, Dec. 2008, pp. 1408-1417.

Simon et al., "Micromachined Metal Oxide Gas Sensors: Opportunities to Improve Sensor Performance" Sensors and Actuators, B 73, 2001, pp. 1-26.

Parameswaran, et al., "Micromachined Thermal Radiation Emitter from a Commercial CMOS Process" IEEE Electron Device Letters, vol. 12, No. 2, Feb. 1991, pp. 57-59.

San et al., "A Silicon Micromachined Infrared Emitter Based on SOI Wafer" Proc. of SPIE, vol. 6836, 2008, 8 pages.

Partial Search Report dated Aug. 21, 2017 for corresponding International Application No. PCT/GB2017/051468.

* cited by examiner

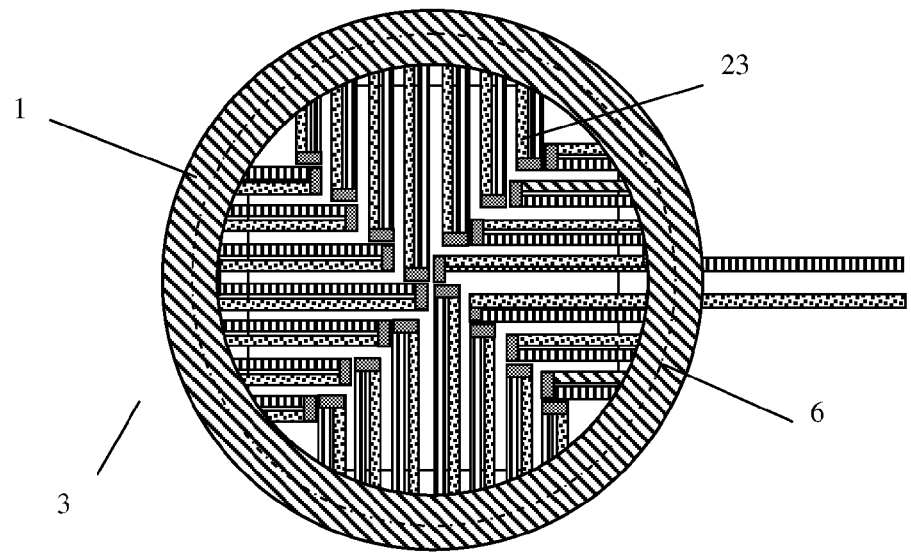
Figure 21
Figure 22(a)
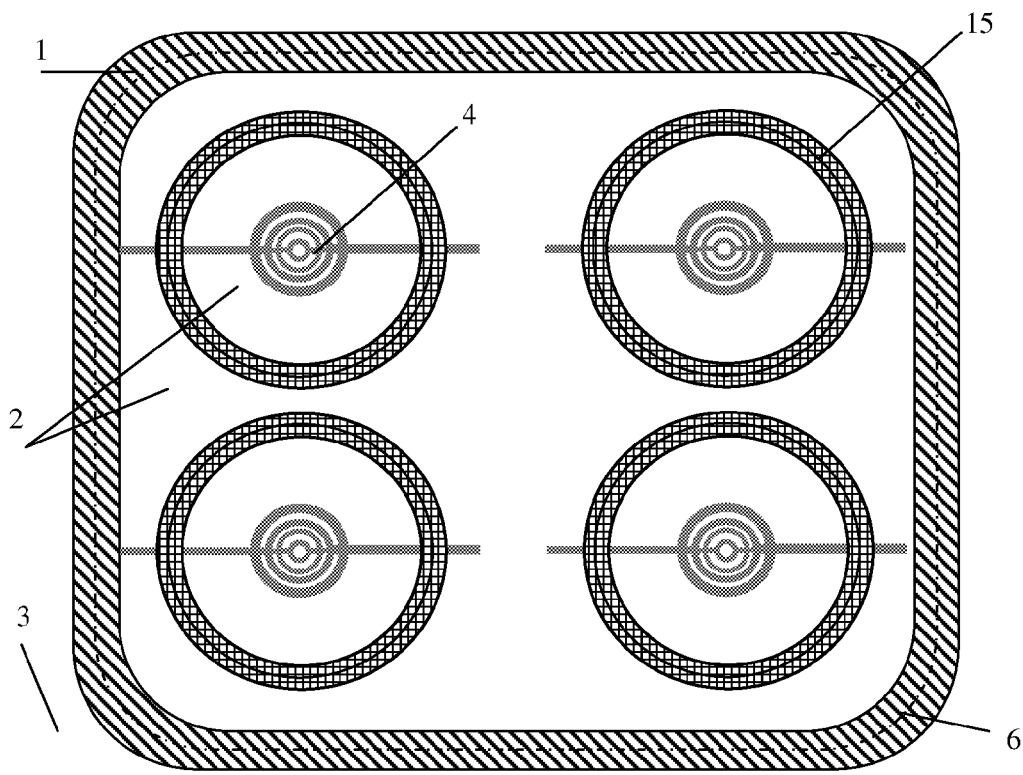

United States Patent US 10,488,358 B2

MICRO-HOTPLATE DEVICES WITH RING STRUCTURES

FIELD OF THE INVENTION

This invention relates to a semiconductor device and a method of manufacturing a semiconductor device, based on micro-hotplates, particularly but not exclusively, for gas sensors. The invention relates to optical emitting sources that includes, but not limited to, Infra-Red (IR), visible and ultra-violate (UV) sources, and the manufacturing method of such sources based on CMOS process.

BACKGROUND OF THE INVENTION

Micro-hotplate structures can be fabricated on a semiconductor substrate and these devices are commercially manufactured. Such structures include a micro-heater embedded within a thin dielectric membrane of a dielectric region, typically comprising silicon dioxide and/or silicon nitride. The membrane of the micro-heater is produced by both wet and dry etching of the semiconductor substrate from the backside or front-side.

A reasonably comprehensive background in a paper entitled "Technological Journey Towards Reliable Microheater Development for MEMS Gas Sensors: A Review", published in the IEEE TRANSACTIONS ON DEVICE AND MATERIALS RELIABILITY, VOL. 14, NO. 2, June 2014, page 589 to 599, gives a good summary of the technology. This review paper identifies issues such as materials, geometry and reliability of micro-heaters and how they are being addressed.

Most of the micro-hotplate devices reported in the literature are not fabricated in a standard microelectronics technology. The microelectronics technology is referred to in a generic form as CMOS technology as this is a well-established technology to fabricate Integrated circuits.

The CMOS term is well known in microelectronics field. In its wide meaning, it refers to the silicon technology for making integrated circuits. CMOS ensures very high accuracy of processing identical transistors (up to billions), high volume manufacturing, very low cost and high reproducibility at different levels (wafer level, wafer to wafer, and lot to lot). CMOS comes with high standards in quality and reliability.

There are many books and articles describing CMOS and there are many variants of CMOS technologies and devices that can be fabricated using CMOS technology. A very basic reference to CMOS can be found in Wikipedia (https://en.wikipedia.org/wiki/CMOS): Complementary metal-oxide-semiconductor (CMOS) is a technology for constructing integrated circuits. CMOS technology is used in microprocessors, microcontrollers, static RAM, and other digital logic circuits, CMOS technology is also used for several analog circuits such as image sensors (CMOS sensor), data converters, and highly integrated transceivers for many types of communication. Frank Wanlass patented CMOS in 1963 (U.S. Pat. No. 3,356,858). Besides digital applications, CMOS technology is also used in analog applications. For example, there are CMOS operational amplifier ICs available in the market, Transmission gates may be used instead of signal relays. CMOS technology is also widely used for RF circuits all the way to microwave frequencies, in mixed-signal (analog and digital) applications.

There are some reports of CMOS based micro-hotplates. For example, Suehle. et. al. "Tin Oxide Gas Sensor Fabricated Using CMOS Micro-hotplates and In-Situ Processing," IEEE Electron Device Letters 1993, F. Udrea et. al. "Design and simulations of SOI CMOS micro-hotplate gas sensors," Sensors and Actuators B 2001, M. Afridi Et. al, "A monolithic CMOS Microhotplate-Based Gas Sensor System," IEEE Sensors Journal 2002, U.S. Pat. No. 5,464,966, M. Graf "CMOS microhotplate sensor system for operating temperature up to 500° C." Sensors and Actuators B 2005, S. Z. Ali et, al, "Tungsten-Based SOI Microhotplates for Smart Gas Sensors" Journal of MEMS 2008, all report different examples of micro-hotplates fabricated in CMOS technology. Other reports by these same groups give information on similar devices, using polysilicon, MOSFETs, Single Crystal Silicon, and tungsten as heater materials.

There are many applications for micro-hotplates that can be found in literature. The most common use of micro-hotplate devices is for gas sensors. Reference to some of these are given in I. Simon et. al, "Micromachined metal oxide gas sensors: opportunities to improve sensor performance," Sensors and Actuators B (2001), and S. Z. Ali Et. Al, "Tungsten-Based SOI Microhotplates for Smart Gas Sensors" Journal of MEMS 2008.

Micro-hotplates are also used as IR emitters. For example, Parameswaran et. al. "Micro-machined thermal emitter from a commercial CMOS process," IEEE EDL 1991, and San et. al. "A silicon micromachined infra-red emitter based on SOI wafer" (Proc of SPIE 2007), describe IR emitter devices based on micro-hotplates on either suspended bridges or membranes One of the main problems with the device fabrication is to maintain accurate tolerance on the size of the dielectric membrane during substrate etching as this can vary between 10-20 um for dry etching, and considerably more for wet etching. The size of the membrane directly affects the electro-thermal properties (such as voltage and power consumption requirements) of the micro-hotplate, as well as device reliability and yield. These problems are identified in literatures, but the method and implications of this variation in terms of the performance of devices and how to address them has never been reported. Specifically, variation in the size of membrane can affect power consumption, thermal mass and residual stress.

It is an object of the present invention to address the problems discussed above.

SUMMARY

Embodiments of the present invention address these problems by placing a combination of single or multi-layer metal, polysilicon layers ring structure that overlaps the dielectric membrane and substrate. The ring structure is designed to take some of the heat via conduction and improved convection and therefore the exact position of the membrane region edge has a smaller effect on the thermal performance (power consumption and thermal mass) when compared to devices without ring.

Similarly, thermopile that makes use of such membrane structures with misaligned, over or under-etching can affect or alter the hot and cold junction uniformity leading to large performance variations in directivity and responsivity of the device.

In accordance with one aspect of the present invention there is provided a micro-hotplate comprising:
   a substrate comprising an etched portion and a substrate portion;
   a dielectric region over the substrate, wherein the dielectric region comprises first and second portions, wherein the first portion is adjacent to the etched portion of the substrate and the second portion is adjacent to the substrate portion of the substrate;

a heater formed in the dielectric region; and a ring structure formed within and/or over the dielectric region such that the ring structure is coupled with the first and second portions of the dielectric region.

The first portion of the dielectric region may be directly adjacent to the etched portion of the substrate and the second portion of the dielectric region may be directly adjacent to the substrate portion of the substrate. It will be appreciated that the first portion of dielectric region is a dielectric membrane region within the dielectric region and therefore in the description below the first portion of the dielectric region may be referred as dielectric membrane or membrane. The first portion or the membrane region is the area in the dielectric region which is directly adjacent or above the etched portion of the substrate. The second portion of the dielectric region is the area of the dielectric region which is directly adjacent or above the substrate portion of the substrate. The ring structure is coupled with both the first portion (the membrane) and the second portion of the dielectric region. It would be appreciated that when the ring structure is coupled with the first and second portions, it is possible that the ring structure only contacts the first portion without extending (or overlapping) into it. The invention covers this scenario as well.

The ring structure may be located along a perimeter (or an edge) of the first portion of the dielectric region and the ring structure is spaced from the heater by the dielectric region. The ring structure generally surrounds the micro-heater.

The ring structure may be located such that the ring structure overlaps with the first portion (or the membrane) and the second portion of the dielectric region.

The ring structure may be formed such that a portion of a width of the ring structure falls within the first portion (or the membrane) of the dielectric region and a remaining portion of the width of the ring structure is located within the second portion of the dielectric region.

The ring structure may be formed such that a portion of a width of the ring structure may be located over the etched portion of the substrate and a remaining portion of the width of the ring structure may be located over the substrate portion of the substrate.

The ring structure may extend through an entire area of the second portion of the dielectric region so that the ring structure extends to a perimeter of an entire chip. The ring structure may extend through the first portion (or the membrane) of the dielectric region to a perimeter (or an edge) of the micro-hotplate.

The ring structure may extend through an entire area of the second portion of the dielectric region so that the ring structure extends to a perimeter of an entire chip.

The ring structure may comprise one or more ring layers.

The ring structure may comprise a first layer which is located at the same level as the heater within the dielectric region.

The ring structure may comprise a second layer which is located at a higher level compared to the heater within the dielectric region.

The ring structure may comprise a third layer which is located at a higher level compared to the heater within the dielectric region.

The ring structure may comprise first, second and third layers stacked over one another within the dielectric region.

The ring structure may be located under the heater.

The one or more layers may comprise a material selected from: a metal selected from aluminium, tungsten, titanium, copper and a combination of any of these materials; and polysilicon, single crystal silicon, a silicide and a combination of any of these materials.

The one or more ring layers may be formed using CMOS or SOI-CMOS technique.

The one or more layers may be formed using a non-CMOS technique.

The ring structure may comprise at least two metal layers stacked over one another within the dielectric region.

The micro-hotplate may further comprise an inter-metal contact between said at least two metal layers.

The micro-hotplate may further comprise a pad layer over the ring layers.

The micro-hotplate may further comprise a post processed metal layer over the ring layers.

The inter-metal contact may be located in the second portion of the dielectric region over the substrate portion of the substrate.

The micro-hotplate may comprise a further inter-metal contact which is located in the first portion of the dielectric region over the etched portion of the substrate.

The inter-metal contact extends in the first and second portions of the dielectric region over the etched and substrate portions of the substrate.

The micro-hotplate may further comprise an auxiliary ring structure between the heater and the ring structure, the auxiliary ring structure being located within the first portion of the dielectric region.

The auxiliary ring structure and the ring structure may be coupled using a plurality of support structures.

The micro-hotplate may further comprise circuitry integrated on the same chip.

The ring structure may have a circular or rectangular shape.

The micro-hotplate may further comprise an electrode layer over the first portion of the dielectric region.

The micro-hotplate may further comprise a sensing material over the electrode layer.

The micro-hotplate may be an environmental sensing device.

The etched portion of the substrate may be formed using an etching technique for back-etching the substrate, the etching technique being selected from a group comprising deep reactive ion etching (DRIE), anisotropic or crystallographic wet etching, potassium hydroxide (KOH) and tetramethyl ammonium hydroxide (TMAH).

The etched portion of the substrate may be formed using a front etching technique.

The substrate may be a semiconductor substrate. The substrate may generally be made of for example:

1) semiconductor
2) Silicon
3) Ceramics (silicon carbide)
4) Polymers (polyester, polyimide, etc. especially for flexible electronics)
5) Metal (this can be used for MEMS)

The first portion of the dielectric region may form a dielectric membrane region.

The micro-hotplate may further comprise at least one patterned layer formed within or on the first portion of the dielectric region. The at least one patterned layer may comprise laterally spaced structures.

The at least one patterned layer may be located over or under the heater.

The micro-hotplate may further comprise a plurality of heaters formed within the first portion of the dielectric region.

Each heater may be surrounded by an auxiliary ring structure formed within the first portion of the dielectric layer.

An array of micro-hotplates may incorporate the micro-hotplate as described above In embodiments, the presence of the ring structure ensures better electro-thermal reproducibility (maximum and average temperature in micro-hotplates vs electrical power) from device to device within the same wafer at different locations, from wafer to wafer and from lot to lot. The electro-thermal properties of the micro-hotplate depend on the membrane size, as the membrane edge acts as a heat sink. However, the membrane etching can vary by 10-20 µm or vary more from device to device. A ring structure within the dielectric membrane on the other hand can be formed using processes with much better tolerances (<2 µm) than the bulk etching of the semiconductor substrate. If the ring has a much higher thermal conductivity than the dielectric membrane materials the inner edge of the ring will act as a thermal heat sink regardless of the edge of the membrane.

In embodiments, a micro-hotplate may comprise a substrate having an etched portion; a dielectric region over the semiconductor substrate; a resistive heater formed within the dielectric region; and a ring is formed using standard CMOS layer and processing steps.

In further embodiments, there is provided a micro-hotplate comprising: a semiconductor substrate having an etched portion; a dielectric region over the semiconductor substrate; a resistive heater formed within the dielectric region; and a ring extended over substrate area. The semiconductor substrate, the dielectric region, the resistive heater may be formed using a CMOS compatible technique.

It is disclosed that the ring around the membrane overlaps with the substrate in which the micro-machined substrate can be other suitable substrate and not limited to only CMOS compatible techniques.

The device or micro-hotplate may be fabricated using a CMOS process, and hence may comprise a CMOS compatible or usable material. The starting wafer can be a bulk silicon wafer or a silicon-on-insulator (SOI) wafer. The difference between the bulk silicon wafer and the SOI wafer is that the bulk silicon wafer does not have any buried oxide formed within the device structure. Alternately the process used may be a non-CMOS process, allowing the use of material not compatible with CMOS processes. The device could also be fabricated by a mix of CMOS and non-CMOS processes, for example by using a CMOS process first to fabricate part of the device, followed by post-CMOS processes which are not CMOS.

The heater formed within the device may be a resistive heater made from a CMOS compatible or usable material such as polysilicon, aluminium, single crystal silicon, or a high temperature CMOS metal, for example aluminium, copper, molybdenum, tungsten or titanium or a combination of those. The heater can also be a metal oxide semiconductor field effect transistor (MOSFET) heater. The heater may also be formed using a non-CMOS material such as platinum or gold.

In embodiments, there is provided a ring overlapping the membrane and substrate or extended over substrate area is not limited to only micro-hotplate, but equally applicable to devices that use front-side, backside or combination of both etching process.

In further embodiments, an array of rings may be placed on a single membrane where multiple micro-hotplates and/or other devices such as thermopiles, thermal flow sensors can be placed. For example, there may be multiple heaters or an array of heaters on a single membrane. The ring can be on the edge of the membrane. Additionally there can also be an auxiliary (or dummy) ring around each individual heater. In the case of resistive gas sensors, each heater may have individual electrodes and sensing material, or may have a common electrode and sensing material. The sensing materials can be the same or can be different on each heater. Similarly for calorimetric gas sensors there may be common or individual catalyst layers. The heaters can all be same or of different sizes. Heaters with rings can be on the same membrane or on separate membranes on the same chip forming an array of micro-hotplate devices.

It is further disclosed that additional rings can be placed over the membrane for mechanical and thermal stress management that can occur between the membrane and substrate. The rings can be joined together to form a net-like structure that helps to provide additional support to strengthen the membrane and improve the reliability.

The rings may be formed using CMOS materials such as single crystal silicon, polysilicon, a silicide or a metal such as tungsten, aluminium, titanium molybdenum or copper. Non-CMOS metals such as platinum or gold may also be used. The ring may comprise a combination of these materials, and may also comprise more than one layer. In case of more than one layer, the layers may also be connected together with the use of contacts and/or vias. The rings maybe made of the same layer used for the heater, or maybe made from a different layer.

In further embodiments, the final fabricated device may be a resistive gas sensor. In this case, there are electrodes on top of the membrane or below the membrane, and a sensing material is grown or deposited on the electrodes. The electrodes maybe made of any material such as gold or platinum, or CMOS compatible materials such as aluminium, tungsten, titanium, titanium nitride or copper, There may also be additional materials in the electrode layer to improve adhesion, or reduce diffusion to the membrane. The electrode material may be deposited on one side of the membrane, or may be embedded within the membrane with openings in the passivation to allow sensing material to electrically contact the electrodes. The sensing material used can be a metal oxide such as tin oxide or zinc oxide, a combination of metal oxides, a polymer, or a nano-material such as graphene, carbon nanotubes or metal or metal oxide nanowires and nano-nets as well as bio-sensing layers such as enzymes, cell receptors, DNA strands, antibodies etc.). The sensing material may also comprise a combination of these materials. The materials may also include other materials or "doping" to improve the sensing characteristics. The sensor may be partly fabricated in a CMOS technology, with either a bulk silicon starting wafer or a silicon-on-insulator (SOI) wafer.

In another embodiment, the final fabricated device maybe a calorimetric gas sensor. In this case a catalyst such as platinum or palladium is deposited on one side of the membrane.

The dielectric membrane (or the first portion of the dielectric region) itself may be circular, rectangular, or rectangular shaped with rounded corners to reduce the stresses in the corners, but other shapes are possible as well. The membrane as well as the top passivation of the device can either be silicon dioxide, silicon nitride, porous silicon and/or aluminium oxide. The membrane can be a full membrane supported along its entire perimeter by the substrate, Alternately it can be a suspended membrane only supported by two or more beams. In this case the ring is designed to be on the edge of the etched portion of the substrate.

According to a further aspect of the invention, there is provided a semiconductor device comprising: a substrate comprising an etched portion and a substrate portion; a dielectric region over the substrate, wherein the dielectric region comprises first and second portions, wherein the first portion is adjacent to the etched portion of the substrate and the second portion is adjacent to the substrate portion of the substrate; and a ring structure formed within and/or over the dielectric region such that the ring structure is coupled with the first and second portions of the dielectric region.

The semiconductor device may further comprise a heater within the first portion of the dielectric region, the heater being surrounded by the ring structure.

The semiconductor device may further comprise a temperature sensor between the heater and the ring structure. The temperature sensor may have at least a partial ring structure. The semiconductor device may further comprise a diode within the first portion of the dielectric region, the diode being surrounded by the ring structure. The diode may be a temperature sensing diode located between the heater and the ring structure.

The semiconductor device may further comprise a thermopile within the first portion of the dielectric region, the thermopile being surrounded by the ring structure.

According to a further aspect of the present invention, there is provided a method of manufacturing a micro-hotplate, the method comprising:

forming a substrate;

depositing one or more layers of metals and/or dielectric layers to form a dielectric region;

forming a heater in the dielectric region;

forming a ring structure within or over the dielectric region;

etching the substrate to form an etched portion of the substrate and a substrate portion of the substrate, wherein the etching of the substrate provides first and second portions in the dielectric region, wherein the first portion is adjacent to the etched portion of the substrate and the second portion is adjacent to the substrate portion of the substrate; and wherein the ring structure is formed such that the ring structure is coupled with the first and second portions of the dielectric region.

The method may further include fabricating a temperature sensor embedded within the dielectric membrane (or the first portion of dielectric region). This may be a resistive temperature sensor made from a metal, or polysilicon, or single crystal silicon, or can be a diode. Preferably the diode may be made with the same CMOS layer used in the CMOS process to make transistors such as n-channel and p-channel FETs. This example is particularly relevant when the semiconductor structure includes a MOSFET structure manufactured using the CMOS processing steps. The cathode of the diode can therefore be formed by using the source of the drain layers of n-channel MOSFET while the anode of the diode can be formed by using the same source or drain layers of a p-channel MOSFET.

Furthermore, the temperature sensors such as diodes resistors or thermopiles, instead of being directly within the heater region could be placed within the membrane between the ring and the heater to avoid exposing them to high temperature. The temperature measured by the temperature sensor in the relatively cooler part of the micro-hotplate can be used to calculate the heater temperature. However for this the membrane heatsink has to be positioned accurately—something not possible with standard bulk etching techniques. However, it will be much more accurate for the micro-hotplates, diodes resistors or thermopiles with rings as the temperature profile within the membrane could be more accurately predicted and is less affected by the exact location of the membrane etch; whereby there is an optimisation of the extension of the ring inside the membrane, towards the heater (or any other devices), for a good trade-off between (i) power consumption (ii) thermal transient response and (iii) electro-thermal reproducibility, mechanical strength and yield.

The device may also have a heat spreading plate made of metal or polysilicon, or in the case of Silicon on Insulator substrates, the device may have a single crystal silicon plate. The role of the spreading plate is to spread more uniformly the heat and thus improve the uniformity of the temperature in the heater area.

In further embodiments, there is provided a device and a method to fabricate an IR CMOS compatible emitter where the heater is embedded within the dielectric membrane (or the first portion of dielectric region) to form a micro-hotplate with a ring structure as described above. The IR emitter may also have a coating to improve emission, such as carbon or metal blacks. The membrane may also have plasmonic structures (a repeating pattern of holes or dots) to improve the device emission. This method of embodiment is also applicable to thermopile, flow sensor or other devices that can be manufactured on any micro-machined substrate.

In embodiments, the method may integrate analogue or digital CMOS circuitry on the same chip (either the resistive gas sensor, or the IR emitter). This may be achieved because of the use of CMOS technology to fabricate the micro-hotplate. The circuitry may be a drive circuit for the heater, comprising a simple current supply, for example using a current mirror circuit, or a more complex circuit to allow heater drive through a constant voltage, constant current or constant power circuit, or a PWM drive. There may also be circuitry to measure the temperature sensor in the membrane, and additionally using it to have a feedback loop to allow a constant temperature control of the heater. Bidirectional current drive can also be implemented.

Other circuitry may be read-out circuitry for the temperature sensor, or the sensing layer. This may include an amplifier, a filter, as well as an analogue to digital converter. Digital circuits may also be integrated to allow digital processing of the signal. Besides these, an off-membrane (outside the area of the membrane or first portion of the dielectric region) temperature sensor, based on a thermo-diode, a resistive temperature sensor, or Vptat or Iptat circuits may also be integrated.

BRIEF DESCRIPTION OF THE PREFERRED EMBODIMENTS

Some preferred embodiments of the invention will now be described by way of example only and with reference to the accompanying drawings, in which:

FIG. 21 shows the top view of ring overlapping membrane and substrate with for a thermopile structure;

FIG. 22(a) shows a top view of a device with an array of micro-heaters on a single membrane;

Figure 26A:
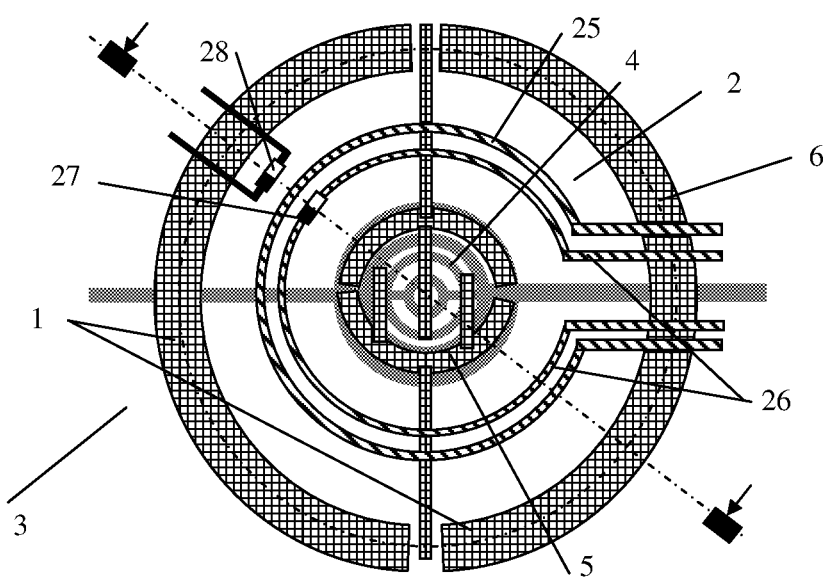
FIG. 26(a) shows top view of an embodiment with a resistive temperature sensing ring.
Figure 26B:
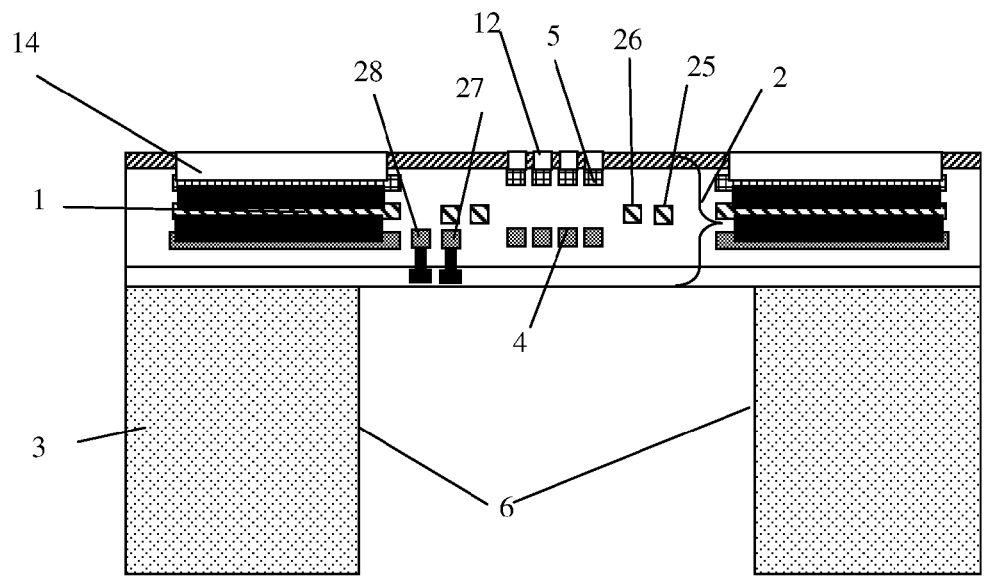
Figure 27:
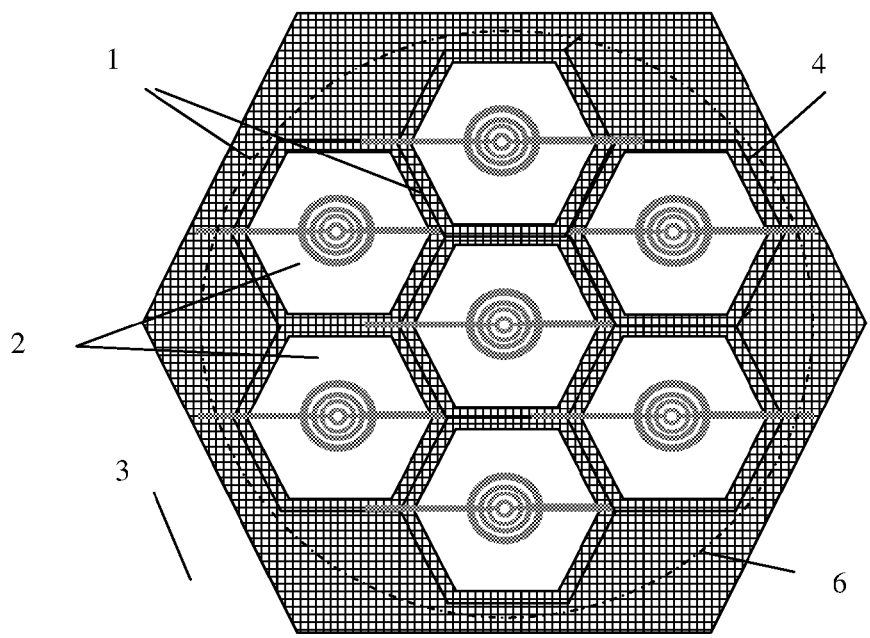
Figure 28:
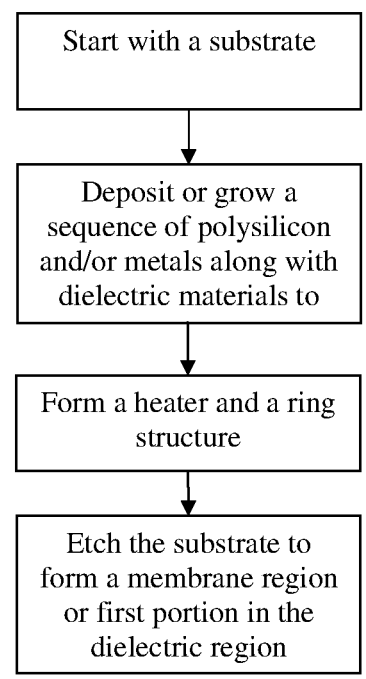

FIG. 26(b) the schematic cross-section of a micro-hotplate with a resistive temperature sensing ring;

FIG. 27 shows top view of hexagonal ring structure with an array of micro-hotplates on the same membrane, and FIG. 28 illustrates an exemplary flow diagram outlining the manufacturing steps of a micro-hotplate in accordance with the present invention.

DETAILED DESCRIPTION OF THE PREFERRED EMBODIMENTS

Embodiments of the invention describe a device designed to eliminate or reduce the effects on the device performance due to misalignment, over or under etching of the substrate by forming a ring which extends partly above the substrate portion supporting the membrane (or the first portion of the dielectric region). The ring could be made in CMOS technology and contain a metal layer such as Al, tungsten, titanium, copper or a combination of those. The ring could be provided by the same layer (using the same mask) as the heater. The ring could be made in CMOS technology and contain a layer of silicon, polysilicon, silicide or a combination of those, whereby the membrane on/in which microelectromechanical (MEMS) devices such as, but not limited to micro-hotplate and thermopiles are manufactured. In this method, the device may be fabricated in a state-of-the-art CMOS process. The process could be either bulk CMOS or SOI CMOS. In the case of micro-hotplate the heater can be made using tungsten, polysilicon, a MOSFET, aluminium or single crystal silicon that is embedded within the membrane (or the first portion of the dielectric region). Similarly, a thermopile, comprising one or more thermocouples connected in series, is embedded within the membrane between the centre and edge of the ring. The thermocouple materials may comprise metal such as Aluminium, Tungsten, Titanium or combination of those, doped polysilicon (n or p type) or doped single crystal silicon (n or p type), All of these layers CMOS compatible.

The wafer on which these devices are manufactured is back-etched using either dry etching through Deep Reactive Ion etching (DRIE) or wet etching using KOH, Preferably the back etch of the membrane is carried out using a Deep Reactive Ion Etch (DRIE). This results in vertical walls and hence reduced area consumption, and additionally good control of the final shape of the membrane, which in turn ensure high reproducibility across the wafer. Alternatively the membrane can be formed by wet etching using for example Potassium Hydroxide (KOH) or TetraMethyl Ammonium Hydroxide (TMAH). This results in a cheaper process.

Ring formation overlapping the membrane and substrate is also applicable for compensating misalignment, over or under etching when front-side etching is used.

In one embodiment, the device and the method described above are not limited to micro-hotplate, but can be applied to other membrane based devices, According to a further embodiment, such a device and the method can be applied to CMOS or non-CMOS based but not limited to resistive gas sensors, infrared emitters, infrared detectors using membranes and MEMS process.

Figure 1:
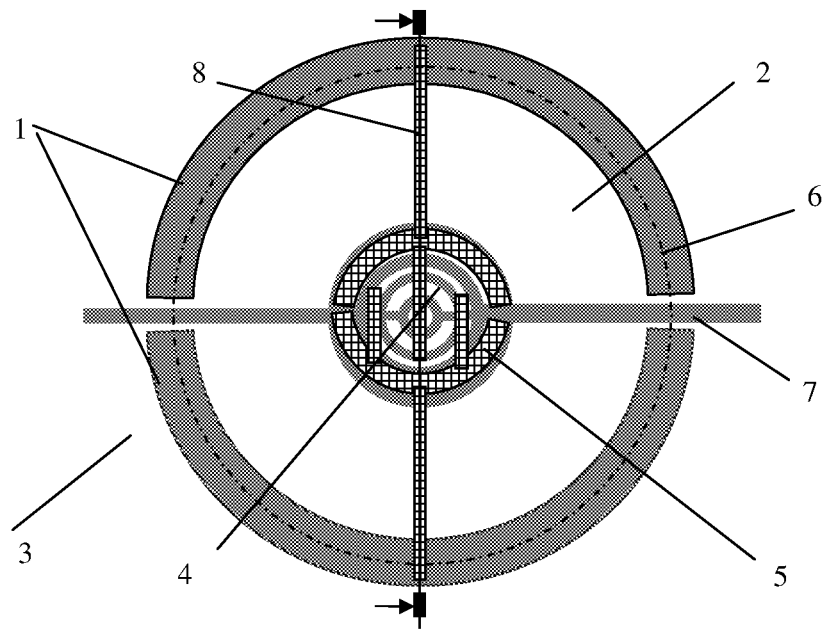
FIG. 1 shows a top view a micro-hotplate with a first metal layer ring overlapping membrane and substrate made in a CMOS SOI process with electrodes for resistive gas sensing.

FIG. 1 shows a top view of a micro-hotplate and electrodes with a first metal layer ring 1 overlapping membrane (or the first portion of the dielectric region) 2 and the end of the etched silicon 6 to the silicon substrate 3 made in a CMOS SOI process with micro-heater 4 and tracks 7 that connects to pads. The micro-hotplate in FIG. 1 also shows electrodes 5 with tracks 8 that connect to pad for resistive gas sensing.

Figure 2:
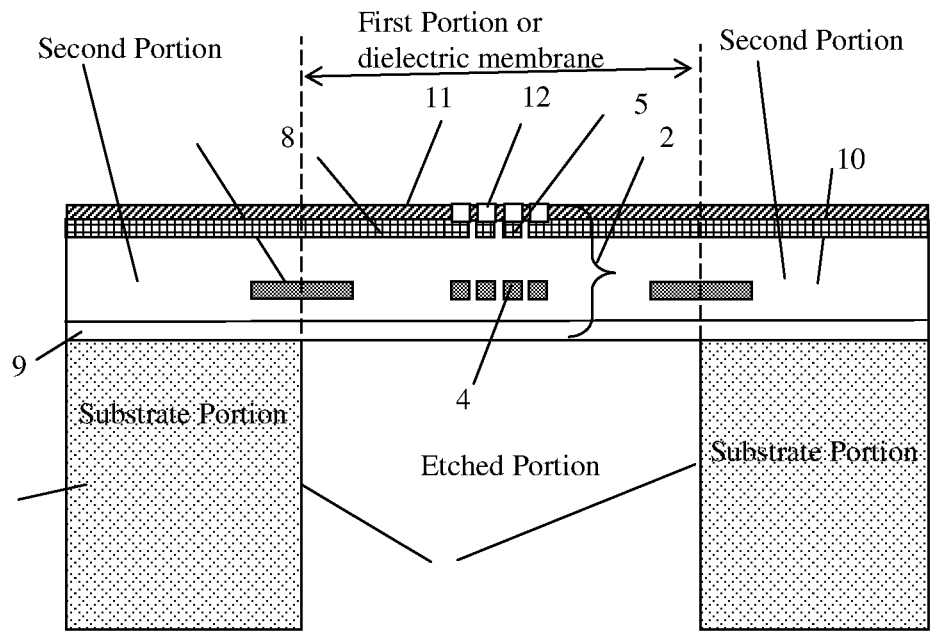
FIG. 2 illustrates a schematic cross-section of the micro-hotplate with a first metal layer ring overlapping membrane and substrate with electrodes for resistive gas sensing.

FIG. 2 shows the schematic cross-section of a micro-hotplate described in FIG. 1 in which the micro-hotplate is made in an SOI process with electrodes for resistive gas sensing. The device comprises a silicon substrate and a dielectric region over the substrate. The substrate has an etched portion and a substrate portion 3 which surrounds the etched portion. The dielectric region comprises a dielectric membrane 2 or the first portion 2 and a second portion adjacent the membrane 2. The second portion is directly above the substrate portion 3 and the membrane 2 is directly adjacent or above the etched portion of the substrate. In FIG. 2, the membrane or the first portion 2 is shown using two dashed-line boundaries. The same definition applies in the remaining figures.

The membrane 2 comprises a buried oxide 9, dielectric layers 10 and passivation layer 11 which are supported by the substrate or the substrate portion 3. A resistive heater 4 is embedded within the membrane 2, and a metal ring 1 that overlapping membrane 2 and the end of the etched silicon 6 to the silicon substrate 3. In other words, the metal ring 1 overlaps with or is coupled with the first portion 2 and the second portion of the dielectric region. On top of the passivation there are passivation opening with electrodes 12, which may be formed of either gold or platinum, or a CMOS metal such as aluminium, tungsten, copper or titanium. This can be used to make contact to the sensing material. The etching is done by deep reactive ion etching (BRIE) to achieve near vertical sidewalls of the trench 6. The layers may be made in a CMOS or a non-CMOS process. It will be appreciated that a standard silicon wafer can be used instead of the SOI wafer. In such a case, the silicon wafer would not have the buried oxide 4 used in the structure of FIG. 2. Alternately a semiconductor other than silicon maybe used as the substrate It will be understood that the semiconductor structure of FIG. 2 can be manufactured using the standard CMOS process. One example of the detailed CMOS manufacturing steps is described as follows:

For the CMOS part of the process to form a simple metal heater (only steps relevant to the fabrication of a simple micro-hotplate are given):

1. The starting substrate is a silicon wafer or an SOI wafer.
2. (only for the case of a starting SOI wafer) Patterning and defining the thin silicon layers, and having oxide in the rest. For the micro-hotplate area the design would typically replace the thin silicon with oxide. However, several other patterns are possible. This can be optionally used to form the ring for the membrane.
3. A layer of dielectric 10 (silicon dioxide or silicon nitride) is deposited across the whole chip (micro-hotplate are and any circuitry).
4. A patterned metal layer is deposited. This forms the micro-heater 4 within the micro-hotplate area. This can be optionally used to form the ring for the membrane.
5. Another layer of dielectric is deposited on top of the micro-heater 4.
6. Another metal layer is deposited. This can optionally be used to form a plate or some other pattern above the heater. This can be optionally used to form the ring for the membrane.
7. Another layer of dielectric is deposited.
8. Another metal layer is deposited. This can optionally be used to form a plate or some other pattern above the heater. This can be optionally used to form the ring for the membrane.
9. A passivation layer 11 of silicon dioxide and/or silicon nitride is deposited.

It will be appreciated that this gives only one sequence of steps, and many other variations are possible and will be obvious to one well versed in the art. The CMOS process may contain other steps (such as p well and/or n well doping, polysilicon deposition, high p+ and n+ doping etc to form a MOSFET)—for a simple device these will not have an effect in the micro-hotplate region, but maybe used to fabricate circuitry on the same chip. The process may also have a different number of metal layers.

Additionally, by varying the use of different layers, the heater can be made of either single crystal silicon (p doped or n doped), or of polysilicon (p doped or n doped), or of one of the other metal layers. The metal layers may have one or more layers or a different material above or below it to improve adhesion and reliability. The device may also have a diode or a resistive temperature sensor made of single crystal silicon, polysilicon or a metal layer.

Figure 3:
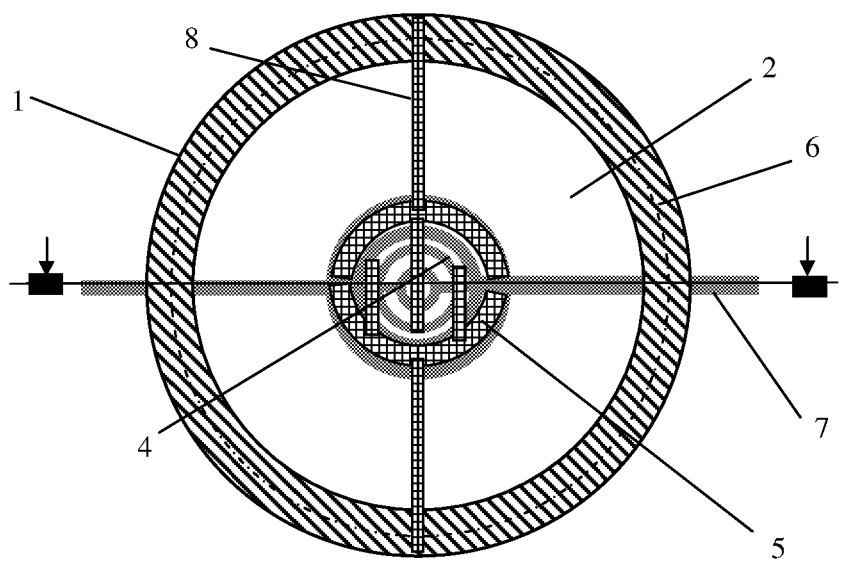
FIG. 3 shows a top view of the micro-hotplate with a second metal layer ring overlapping membrane and substrate with electrodes for resistive gas sensing.

FIG. 3 shows a top view of a micro-hotplate and electrodes with another embodiment that uses a second metal layer ring 1 overlapping membrane (or the first portion of the dielectric region) 2 and the end of the etched silicon 6 to the silicon substrate 3 made in a CMOS SOI process with micro-heater 4 and tracks 7 that connects to pads.

Figure 4:
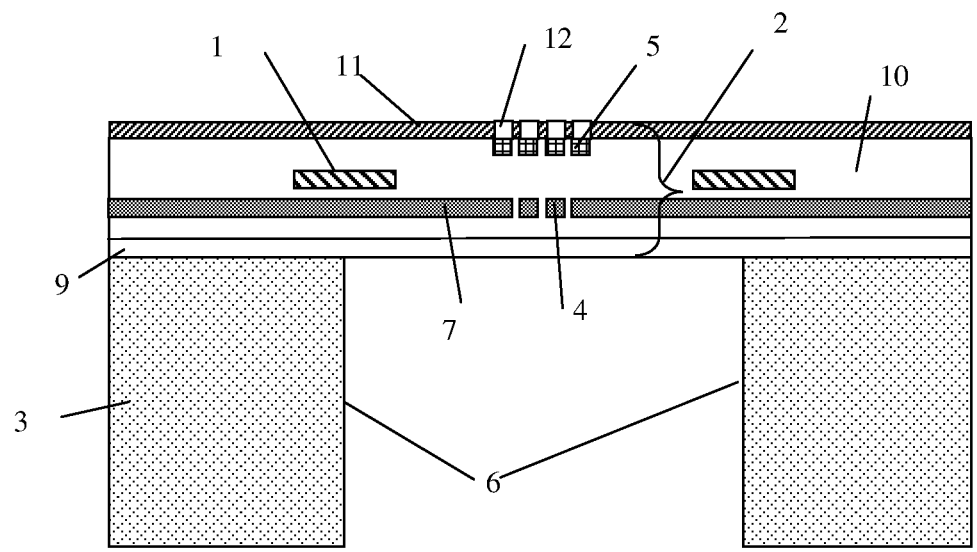
FIG. 4 illustrates a schematic cross-section of the micro-hotplate with a second metal layer ring overlapping membrane and substrate with electrodes for resistive gas sensing.

FIG. 4 shows the schematic cross-section of a micro-hotplate and electrodes described in FIG. 3 whereby it is made in an SOI process with electrodes for resistive gas sensing. The device shows the embodiment with second metal ring 1 that overlaps membrane (or the first portion of the dielectric region) 2 and the end of the etched silicon 6 to the silicon substrate 3 together with micro-heater 4 and tracks 7 that connects to pads.

Figure 5:
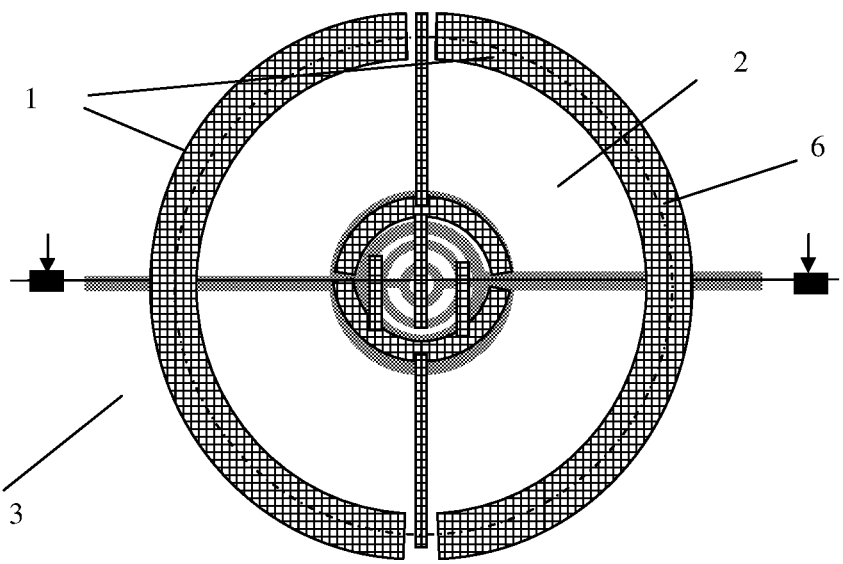
FIG. 5 shows a top view of the micro-hotplate with a top metal layer ring overlapping membrane and substrate with electrodes for resistive gas sensing.

FIG. 5 shows a top view of a micro-hotplate and electrodes with another embodiment that uses a third metal layer ring 1 overlapping membrane 2 and the end of the etched silicon 6 to the silicon substrate 3.

Figure 6:
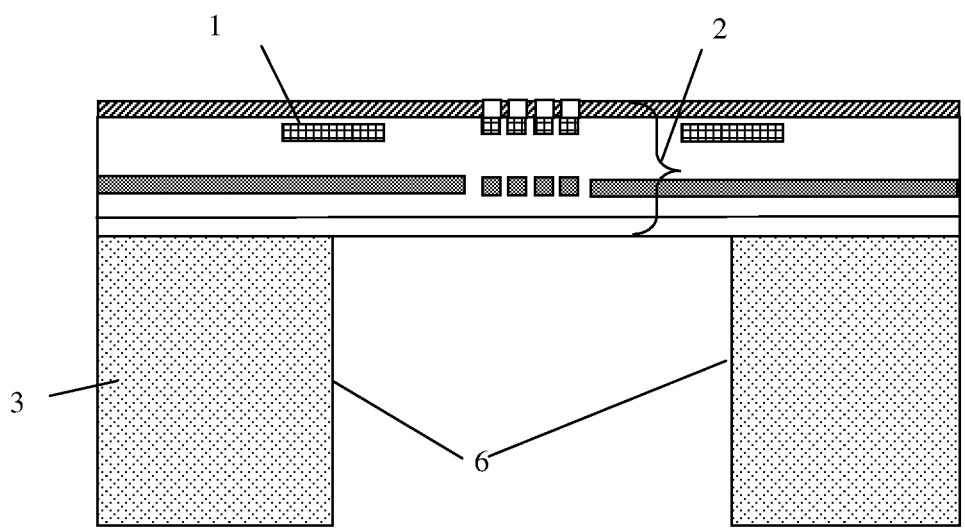
FIG. 6 illustrates a schematic cross-section of the micro-hotplate with a top metal layer ring overlapping membrane and substrate with electrodes for resistive gas sensing.

FIG. 6 shows the schematic cross-section of a micro-hotplate and electrodes described in FIG. 5 whereby it is made in an SOI process with electrodes for resistive gas sensing. The device shows the embodiment with third metal ring 1 that overlaps membrane 2 and the end of the etched silicon 6 to the silicon substrate 3. It will be appreciated that the ring 1 is not limited to the number of layers as this may be defined by the choice of the silicon process node and module selected for the wafer.

Figure 7:
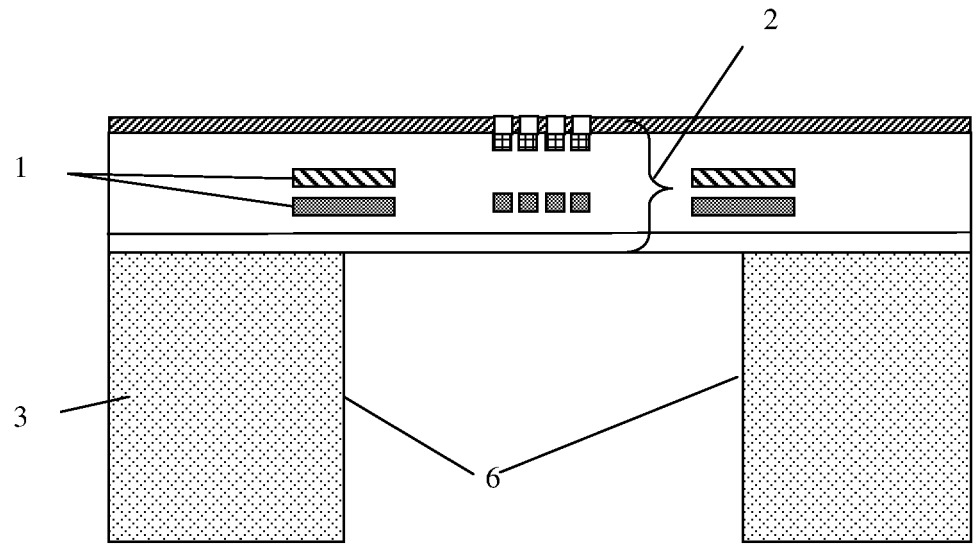
FIG. 7(a) illustrates a schematic cross-section of the micro-hotplate with a combination of metal layer that can be used for the ring overlapping membrane and substrate with electrodes for resistive gas sensing.
FIG. 7(b) illustrates a schematic cross-section of the micro-hotplate with an alternative combination of metal layer that can be used for the ring overlapping membrane and substrate with electrodes for resistive gas sending.
FIG. 7(c) illustrates a schematic cross-section of the micro-hotplate with an alternative combination of metal layer that can be used for the ring overlapping membrane and substrate with electrodes for resistive gas sensing.
FIG. 7(d) illustrates a schematic cross-section of the mirco-plate with an alternative combination of metal layer that can be used for the ring overlapping membrane and substrate electrodes for resistive gas sensing.
Figure 7:
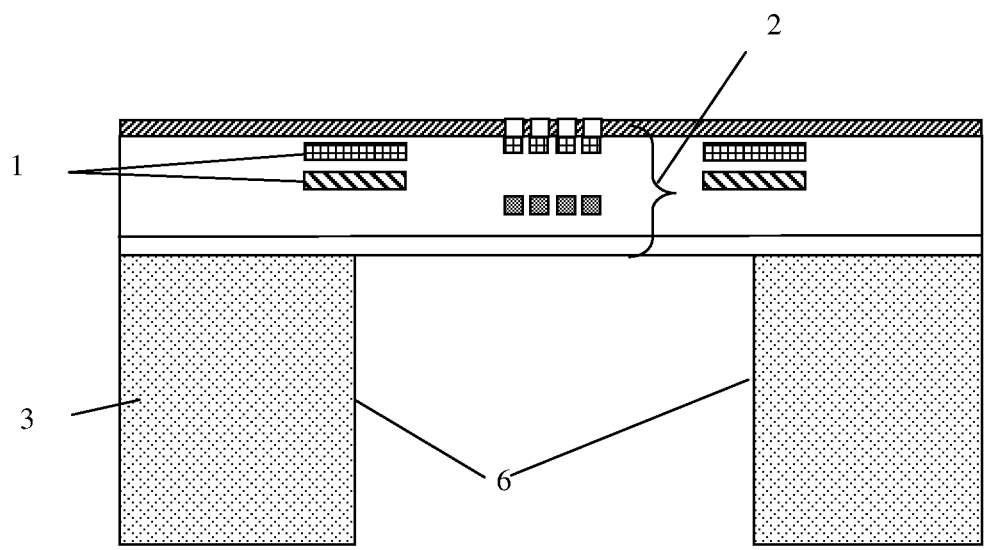
Figure 7:
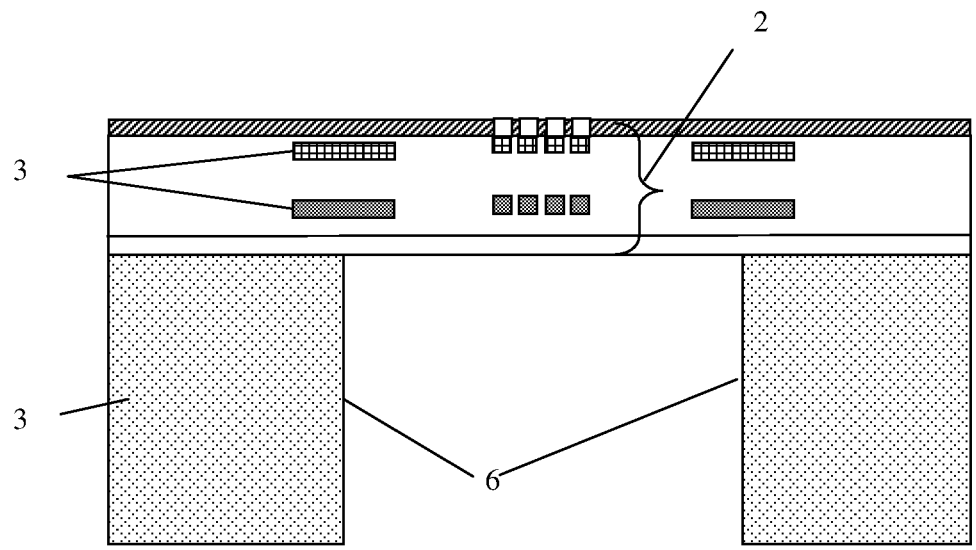
Figure 7:
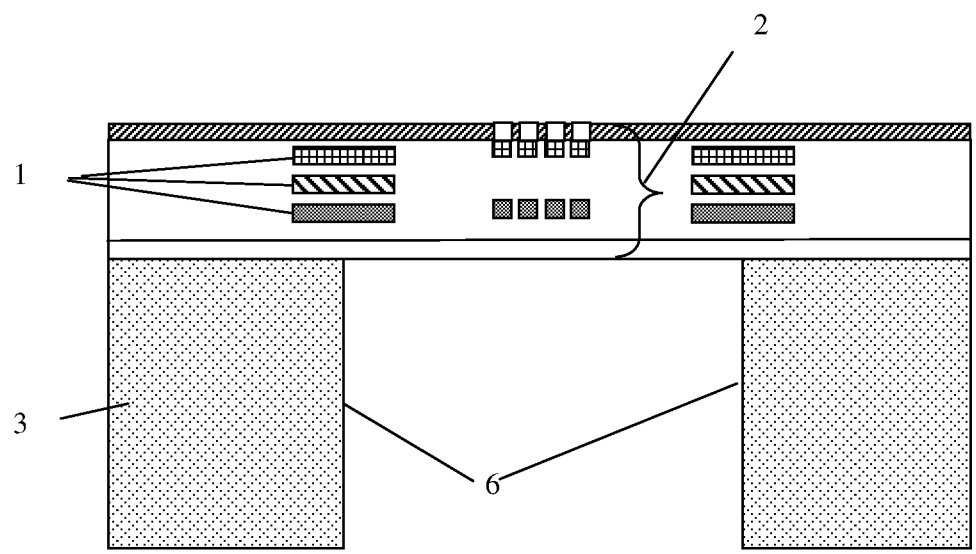

FIG. 7 shows the schematic cross-section of a micro-hotplate with electrodes device and optional combinations of metal layers that can be used for the ring 1 as follows:
(a) It comprises first and second metal layer rings 1, stacked vertically using standard CMOS or non-CMOS processing steps that overlap membrane 2 and the end of the etched silicon 6 to the silicon substrate 3.
(b) It comprises second and third metal layer rings 1, stacked vertically overlapping membrane 2 and the end of the etched silicon 6 to the silicon substrate 3.
(c) It comprises first and third metal layer rings 1, stacked vertically overlapping membrane 2 and the end of the etched silicon 6 to the silicon substrate 3.
(d) It comprises first, second and third metal layer rings 1, stacked vertically overlapping membrane 2 and the end of the etched silicon 6 to the silicon substrate 3.

Figure 8:
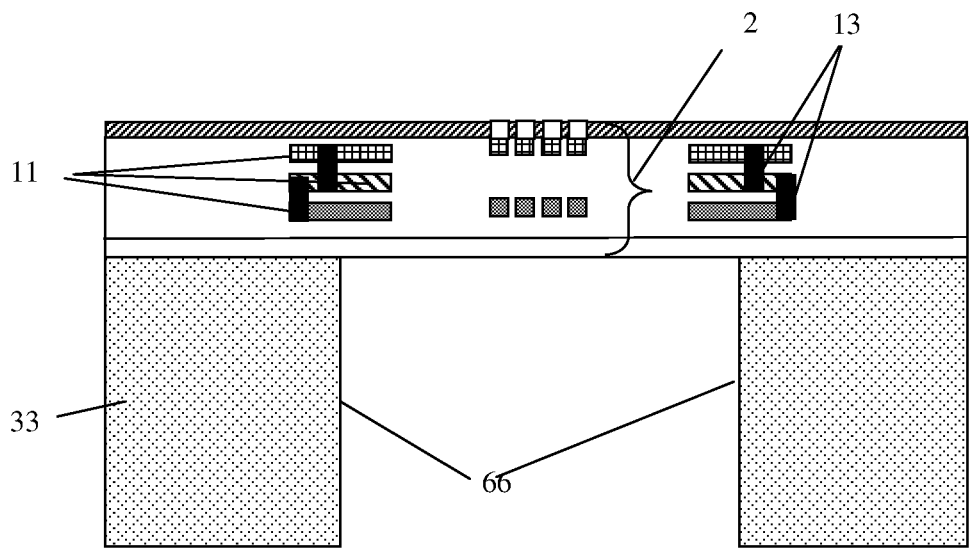
FIG. 8(a) illustrates a schematic cross-section of the micro-hotplate with a combination of metal layer and inter-layer contact that can be used for the ring overlapping membrane and substrate with electrodes for resistive gas sensing.
FIG. 8(b) illustrates a schematic cross-section of the micro-hotplate with an alternative combination of metal layer and inter-layer contact that can be used for the ring overlapping membrane and substrate with electrodes for resistive gas sensing.
FIG. 8(c) illustrates a schematic cross-section of the micro-hotplate with an alternative combination of metal layer and inter-layer contact that can be used for the ring overlapping membrane and substrate electrodes for resistive gas sending.
FIG. 8(d) illustrates a schematic cross-section of the micro-hotplate with an alternative combination of metal layer and inter-layer contact that can be used for the ring overlapping membrane and substrate with electrodes for resistive gas sensing.
Figure 8:
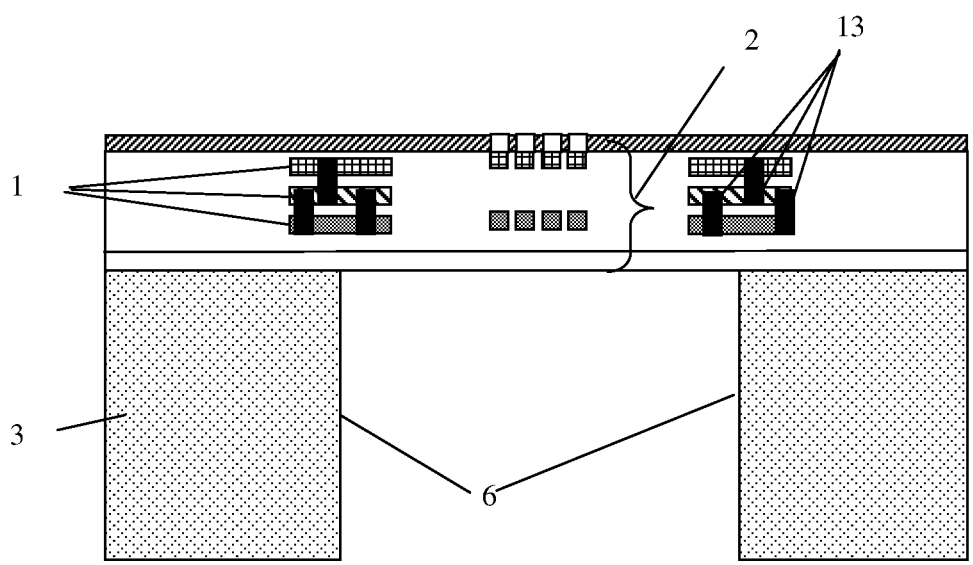
Figure 8C:
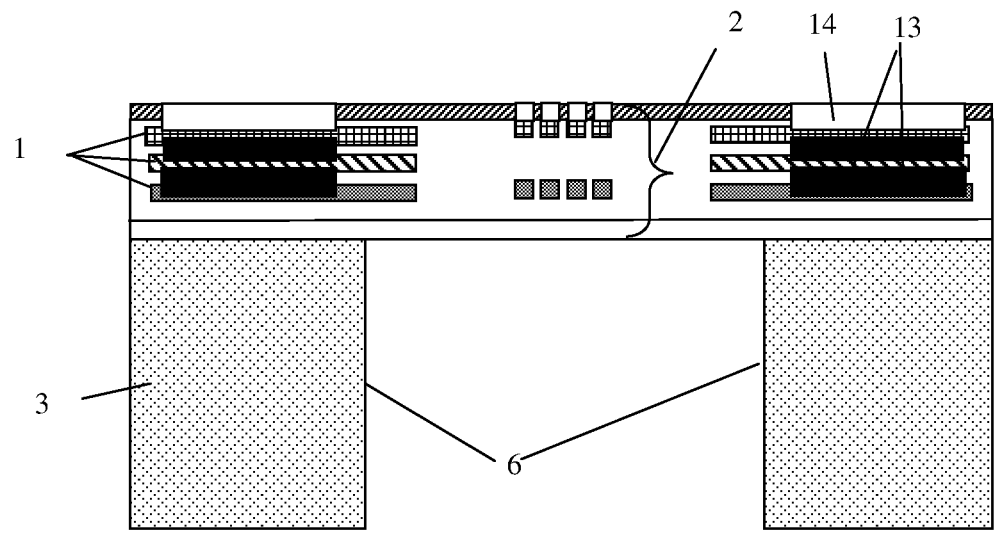
Figure 8D:
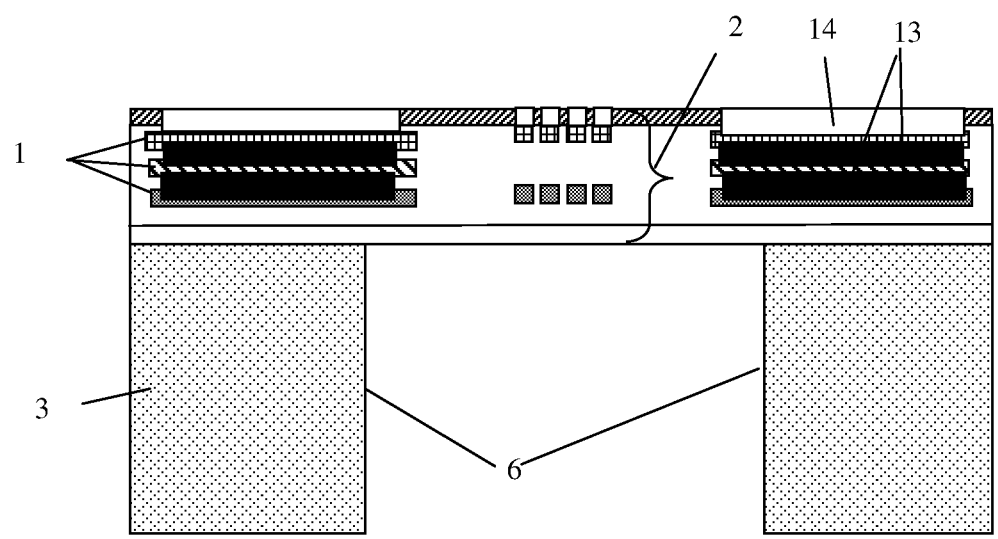

FIG. 8 shows the schematic cross-section of a micro-hotplate device with electrodes and optional combinations of metal layers with inter-metal contacts 13 that can be used for the ring 1 as follows:
(a) It comprises first, second and third metal layer rings 1, stacked vertically with inter-metal contacts 13 using standard CMOS or non-CMOS processing steps that overlaps membrane 2 and the end of the etched silicon 6 to the silicon substrate 3. The inter-metal contacts 13 in this example is placed off the membrane 2, but aligned on top of the silicon substrate 3.
(b) It comprises first, second and third metal layer rings 1, stacked vertically with inter-metal contacts 13 using standard CMOS or non-CMOS processing steps that overlap membrane 2 and the end of the etched silicon 6 to the silicon substrate 3. The inter-metal contacts 13 in this example is placed both on the membrane 2 as well as aligned on top of the silicon substrate 3.
(c) It comprises first, second and third metal layer rings 1, stacked vertically with inter-metal contacts 13 together with pad layer 14 that overlaps membrane 2 and the end of the etched silicon 6 to the silicon substrate 3. The inter-metal contacts 13 and pad layer 14 in this example is placed off the membrane 2, but aligned on top of the silicon substrate 3.
(d) It comprises first, second and third metal layer rings 1, stacked vertically with inter-metal contacts 13 together with pad layer 14 that overlaps membrane 2 and the end of the etched silicon 6 to the silicon substrate 3. The inter-metal contacts 13 and a pad layer 14 in this example are placed both on the membrane 2, as well as on top of the silicon substrate 3.

It should be appreciated that other metal rings 1 with different combination of metals and inter-layer contacts not exclusively shown in FIG. 8, can also be used.

Figure 9:
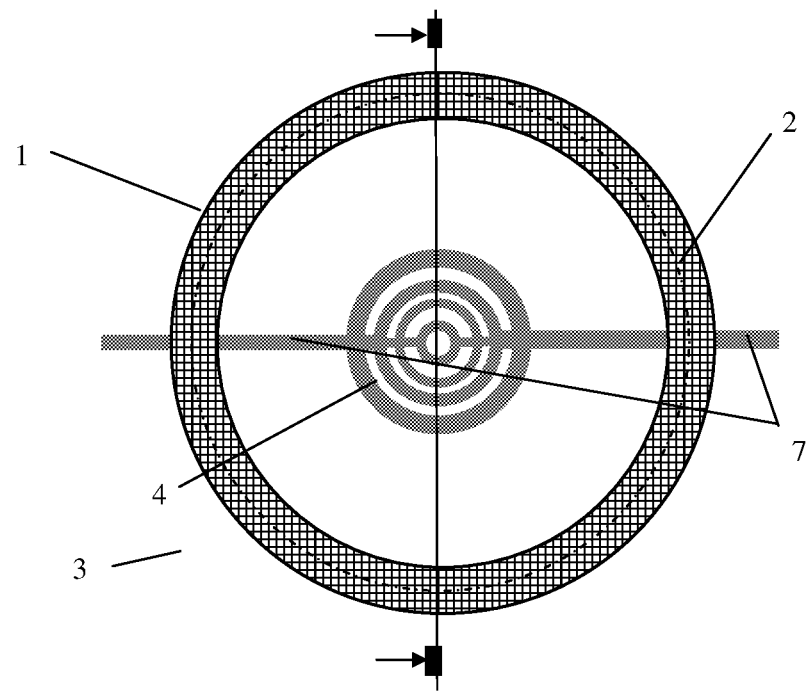
FIG. 9 shows a top view of the micro-hotplate with metal layer ring overlapping membrane and substrate.
Figure 10:
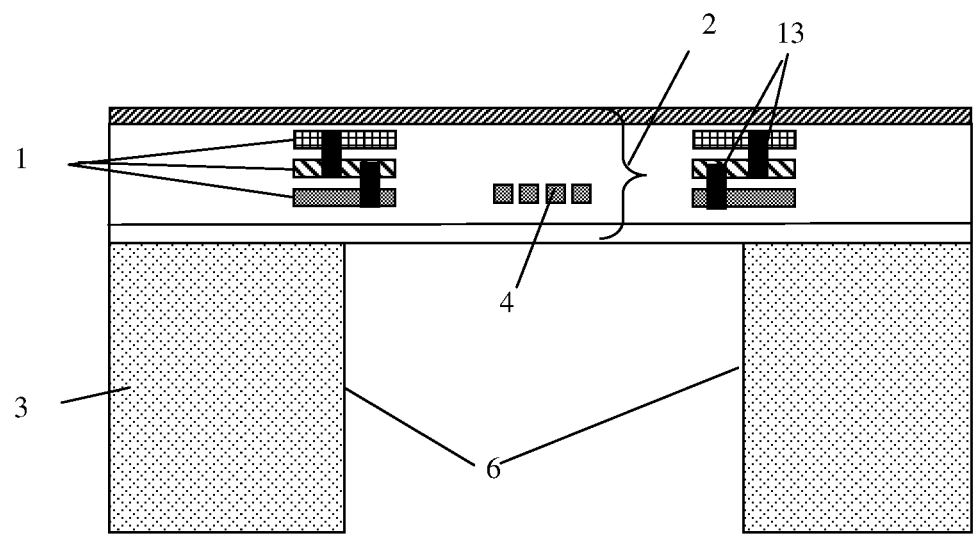
FIG. 10 illustrates a schematic cross-section of the micro-hotplate with alternative combinations of metal layer and inter-layer contact that can be used for the ring overlapping membrane and substrate.

FIG. 9 shows an example of a top view of a micro-hotplate without electrodes and with a metal layer ring 1 overlapping membrane 2 and the end of the etched silicon 6 to the silicon substrate 3 made in a CMOS SOI process with micro-heater 4 and tracks 7 that connects to pads. Such a device can be used for example as an IR emitter or a calorimetric gas sensor FIG. 10 shows the schematic cross-section of a micro-hotplate described in FIG. 9. The device illustrates the embodiment with first, second and third metal layer rings 1, stacked vertically with inter-metal contacts 13 using standard CMOS or non-CMOS processing steps that overlap membrane 2 and the end of the etched silicon 6 to the silicon substrate 3. The inter-metal contacts 13 in this example can be on or off (outside) the membrane 2, as well as on top of the silicon substrate 3. Furthermore, the same combination of ring 1 structure as described in FIG. 8 can be used.

Figure 11:
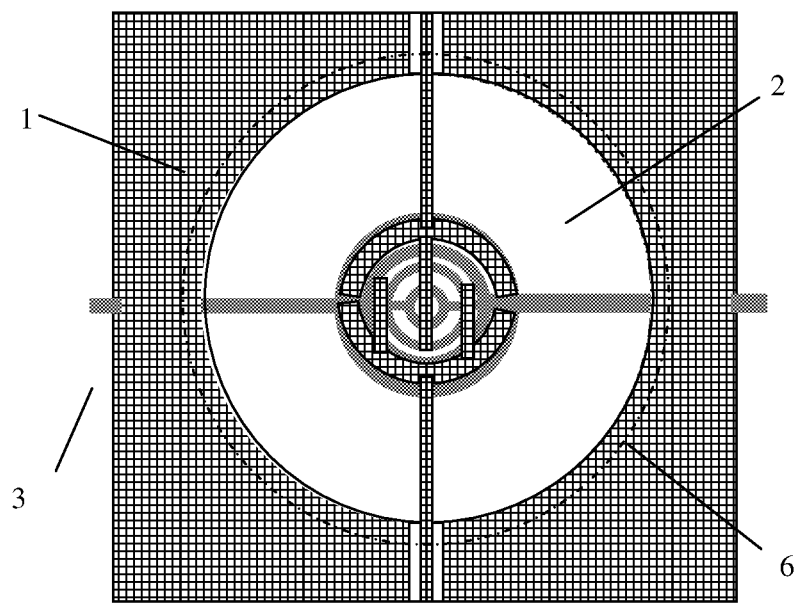
FIG. 11 shows a top view of the micro-hotplate with metal layer ring overlapping membrane and substrate and extended cover of the metal layers over the substrate.

FIG. 11 shows another embodiment of a top view of a micro-hotplate based device with extended metal layer rings 1 overlapping membrane 2 and the end of the etched silicon 6 to the silicon substrate 3.

Figure 12:
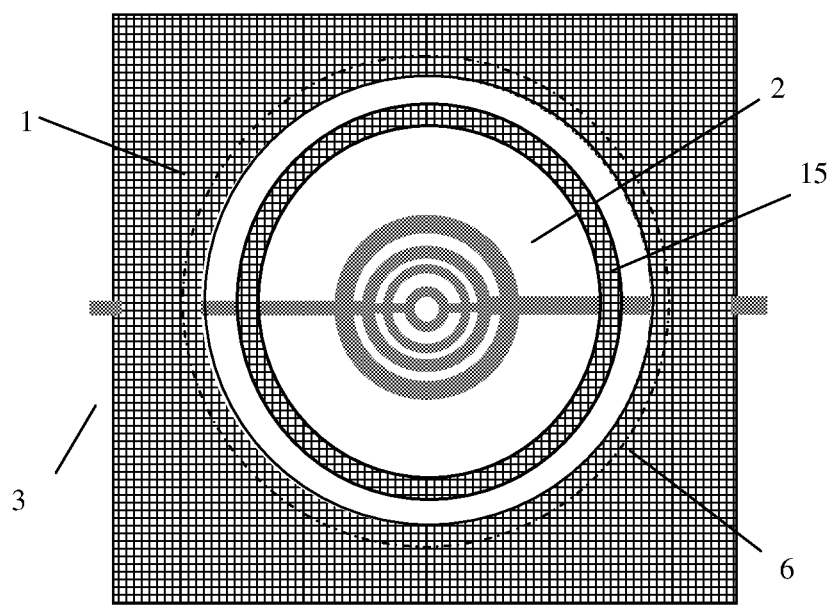
FIG. 12 shows a top view of the micro-hotplate with metal layer ring overlapping membrane and substrate and dummy internal ring together with extended cover of the metal layers over the substrate.

FIG. 12 shows another embodiment of a top view of a micro-hotplate based device with extended metal layer rings 1 overlapping membrane 2 and the end of the etched silicon 6 to the silicon substrate 3. It also shows a dummy (or auxiliary) metal ring 15 placed entirely on the membrane, where the spacing between the rings can be selected according to a specific design requirement. It should be appreciated that there can be more than one dummy (or auxiliary) rings 15 can be placed on the membrane 2 and any combination of metal stacking with or without inter-metal contacts can be used as described in FIG. 7 and FIG. 8.

Figure 13:
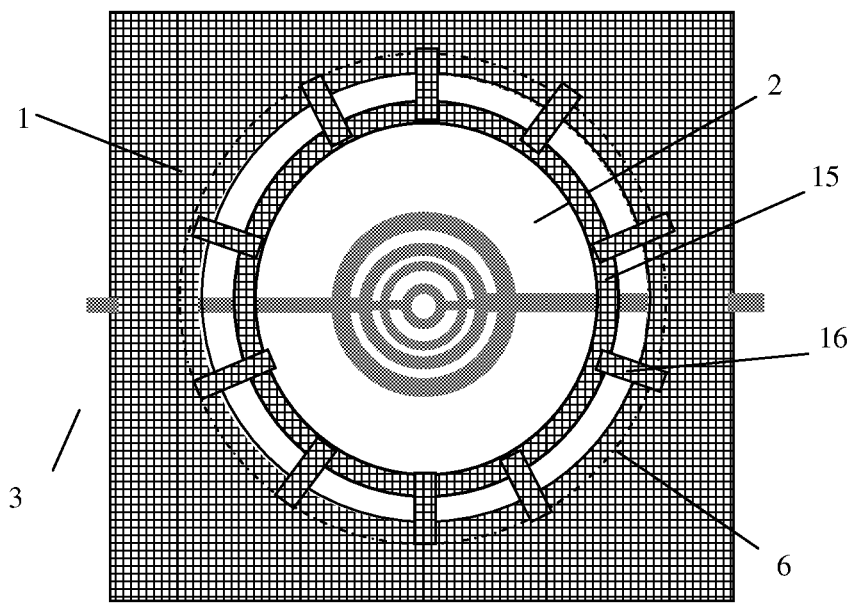
FIG. 13 shows a top view of the micro-hotplate with metal layer ring overlapping membrane and substrate and dummy internal ring and additional metal strapping together with extended cover of the metal layers over the substrate.

FIG. 13 shows another embodiment of a top view of a micro-hotplate based device with extended metal layer rings 1 overlapping membrane 2 and the end of the etched silicon 6 to the silicon substrate 3. It also shows a dummy (or auxiliary) metal ring 15 placed entirely on the membrane, that is attached using the same metal layer to the inner ring 1 where the spacing between the rings can be selected according to a specific design requirement.

Figure 14:
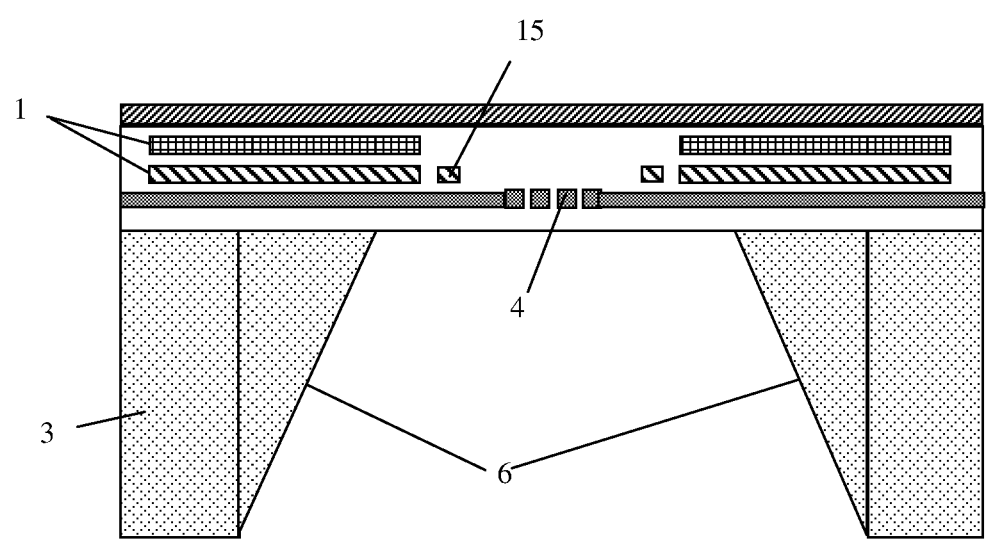
FIG. 14 illustrates a schematic cross-section of an alternative micro-hotplate process with metal layer ring overlapping membrane and substrate made in a CMOS process, where the back etching is done by KOH etching.

FIG. 14 shows a micro-hotplate device with a ring 1, where the back etching has been perform by wet etching (for example using KOH or TMAH). This results in slanting sidewalls of the trench 6, as opposed to the vertical sidewalls created by DRIE. It should be appreciated that all different types and combinations of embodiments of the rings 1 and rings 15 as described in this invention disclosure is equally applicable to this wet etching option.

Figure 15:
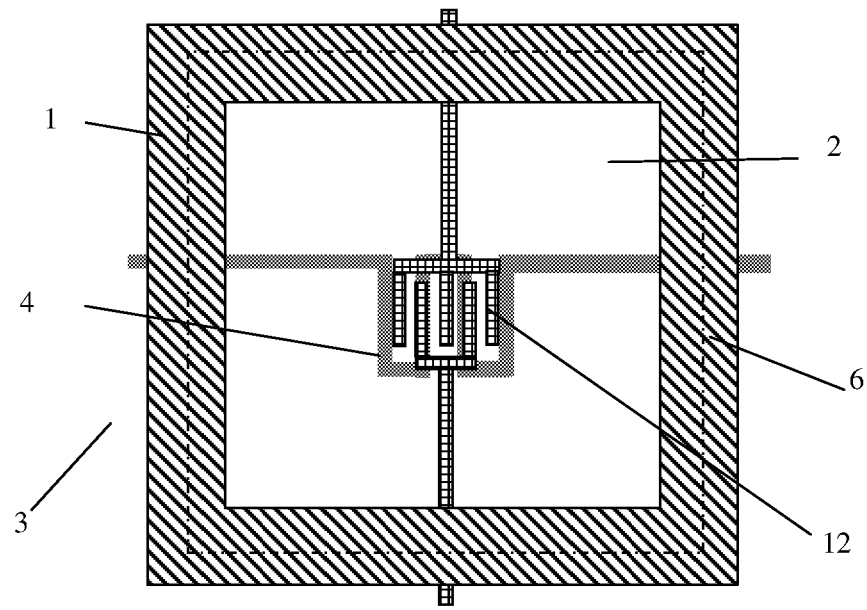
FIG. 15 shows a top view of a square micro-hotplate with metal layer ring overlapping membrane and substrate.

FIG. 15 shows a top view of a micro-hotplate based device where the embodiment of the ring 1 is a square in shape. The ring 1 overlaps the membrane (or the first portion of the dielectric region) 2 and the end of the etched silicon 6 of the silicon substrate 3. The micro-heater 4 and the electrodes 12 can be similarly shaped as required. It should be appreciated that the embodiments of the ring 1 can be of any shape to match or otherwise and not limited to circular or square shape of the membrane 2, It should further be appreciated that all design variation of the embodiments of the ring 1 is applicable to any shapes and size of the membrane 2.

Figure 16:
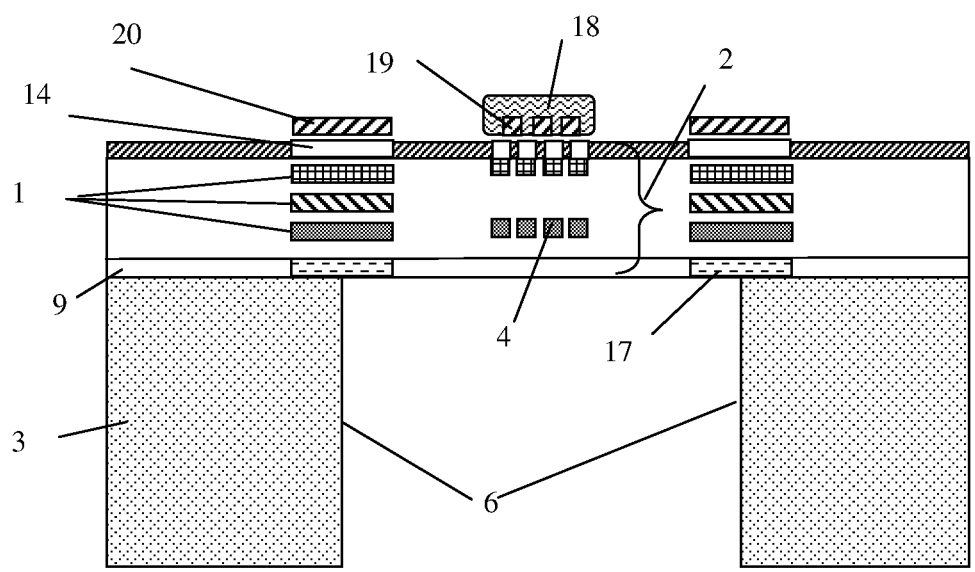
FIG. 16 illustrates a schematic cross-section of micro-hotplate with metal layer and buried SOI layer ring overlapping membrane and substrate with all possible Interdigitated electrodes (IDES) structure on the sensing area of the membrane.

FIG. 16 shows the schematic cross-section of a micro-hotplate with sensing material 18 and post-CMOS process electrodes 19 with a stack of ring 1 layers. The device illustrates the embodiment of the ring 1 with first, second and third metal layers, stacked vertically together with stack of layers in the buried oxide for SOI process as well as post-CMOS process layer that can be placed on the pad 14 or without the pad 14. The embodiment of the ring can be contacted using inter-metal contacts as described in FIG. 8 using standard CMOS or non-CMOS with or without post-processed metal layer 20 that overlap membrane 2 and the end of the etched silicon 6 to the silicon substrate 3. There is also provided a polysilicon ring structure 17 under the heater 4.

Figure 17:
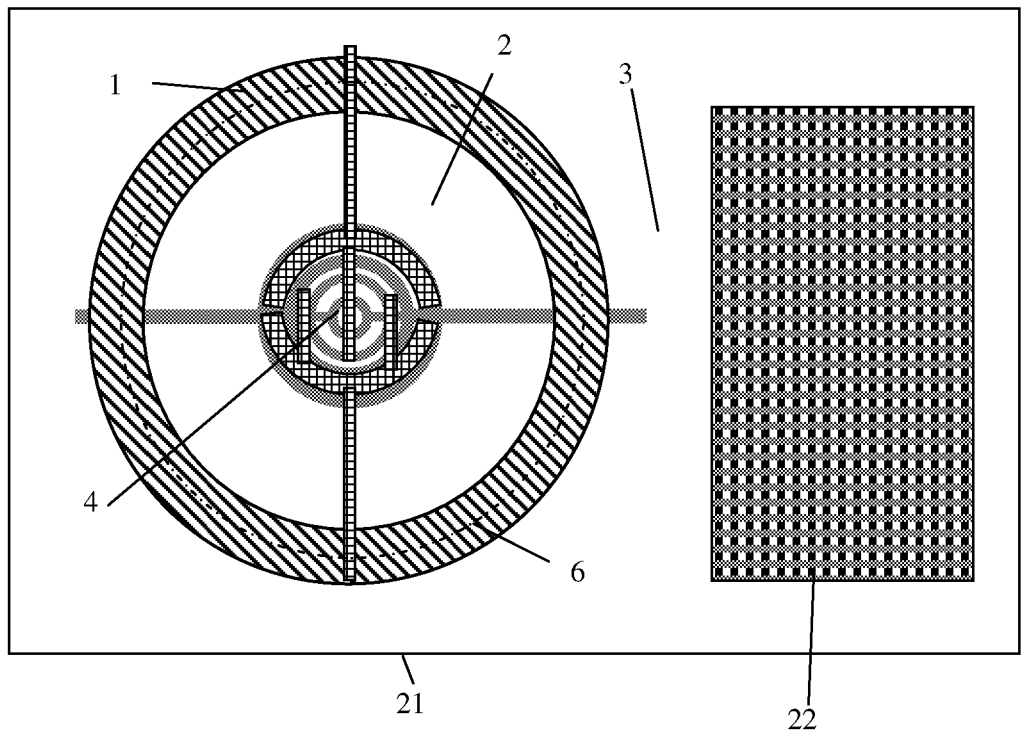
FIG. 17 shows the top view of a CMOS chip with micro-hotplates and ring overlapping membrane and substrate based gas sensors and interface circuitry on the same chip.

FIG. 17 shows a top view of a silicon chip 21 with ring 1 that overlaps the membrane 2 and the end of the etched silicon 6 to the silicon substrate 3. Using standard CMOS or SOI-CMOS process, integrated electronic circuits 22 can be manufactured on the same device.

Figure 18:
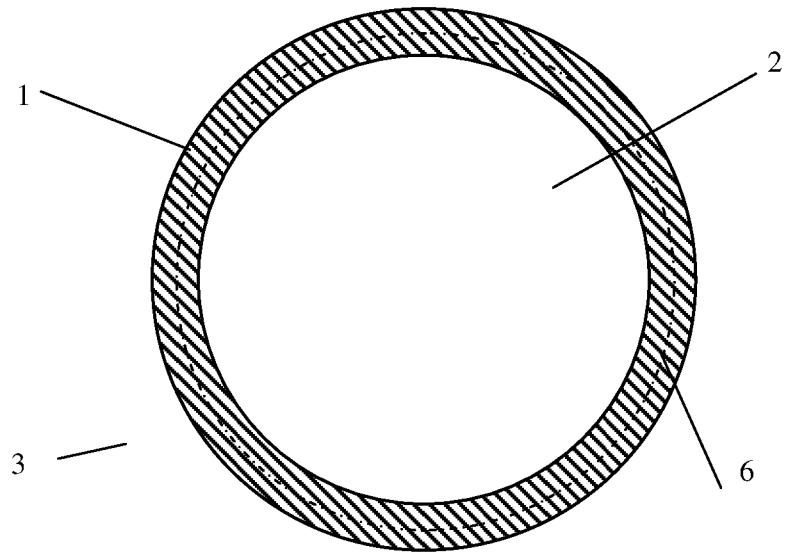
FIG. 18 shows the top view of ring overlapping membrane and substrate.

FIG. 18 shows a top view of a device with a ring 1 that overlaps the membrane 2 and the end of the etched silicon 6 to the silicon substrate 3. The membrane 2 may have any device, structures or none as may be desired. The embodiment of the ring 1 can take any of the structures as described in FIG. 7 and FIG. 8.

Figure 19:
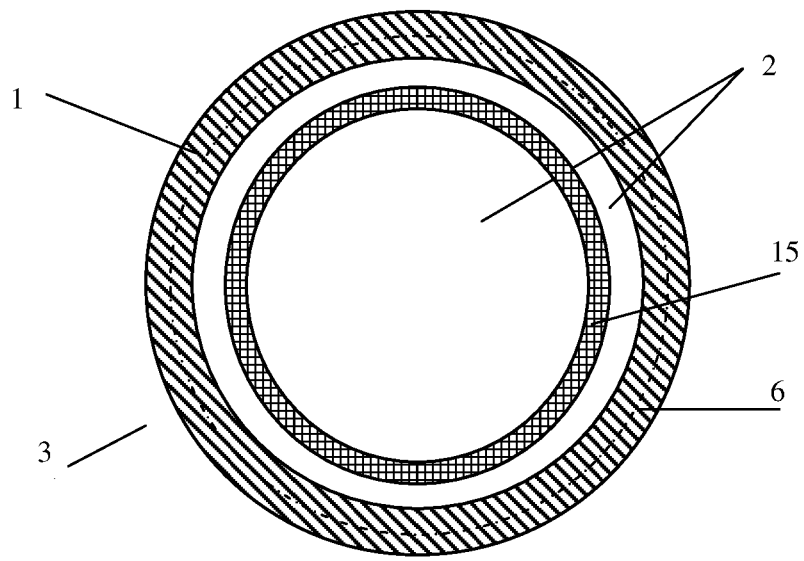
FIG. 19 shows the top view of ring overlapping membrane and substrate and dummy internal ring.

FIG. 19 shows a top view of a device with a dummy (or auxiliary) ring 15 and a ring 1 that overlaps the membrane 2 and the end of the etched silicon 6 to the silicon substrate 3. The membrane 2 may have any device, structures or none as may be desired. The embodiment of the ring 1 and the dummy (or auxiliary) ring 15 can take any of the structures as described in FIG. 7 and FIG. 8.

Figure 20:
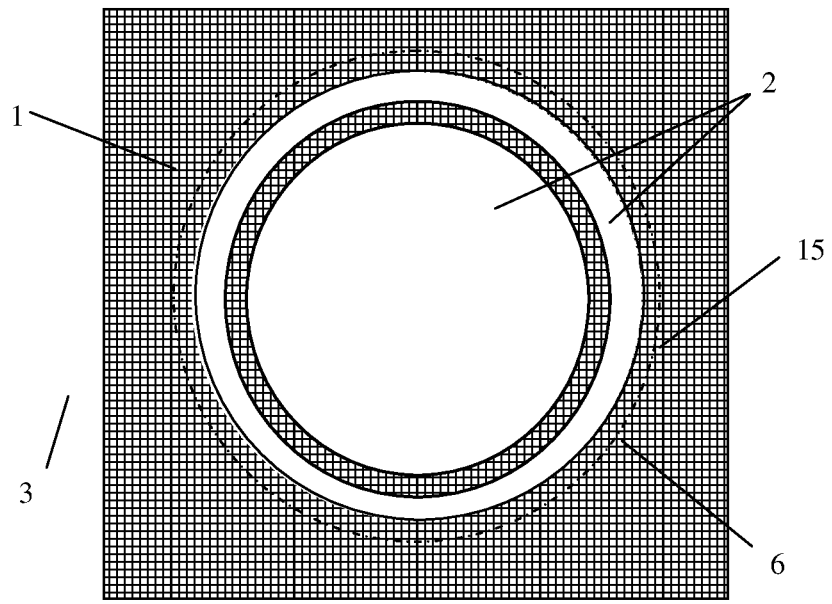
FIG. 20 shows the top view of ring overlapping membrane and substrate with extended metal layer and dummy internal ring.

FIG. 20 shows a top view of a device with a dummy ring 15 and an extended ring 1 that overlaps the membrane 2 and the end of the etched silicon 6 to the silicon substrate 3. The membrane 2 may have any device, structures or none as may be desired. The embodiment of the ring 1 can take any of the structures as described in FIG. 7 and FIG. 8.

FIG. 21 shows a top view of a thermopile 23 with a ring 1 that overlaps the membrane 2 and the end of the etched silicon 6 to the silicon substrate 3. The membrane 2 may have any device, structures or none as may be desired. The embodiment of the ring 1 can take any of the structures as described in FIG. 7 and FIG. 8.

Figure 22B:
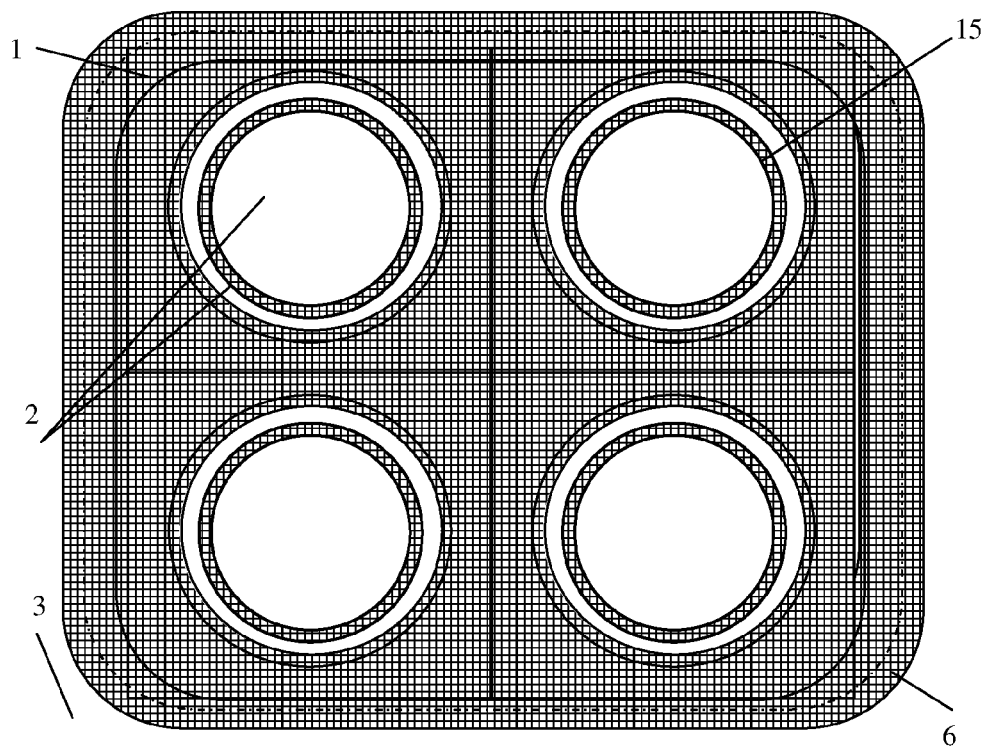
FIG. 22(b) shows a top view with a device with an array of rings on a single membrane.
Figure 22C:
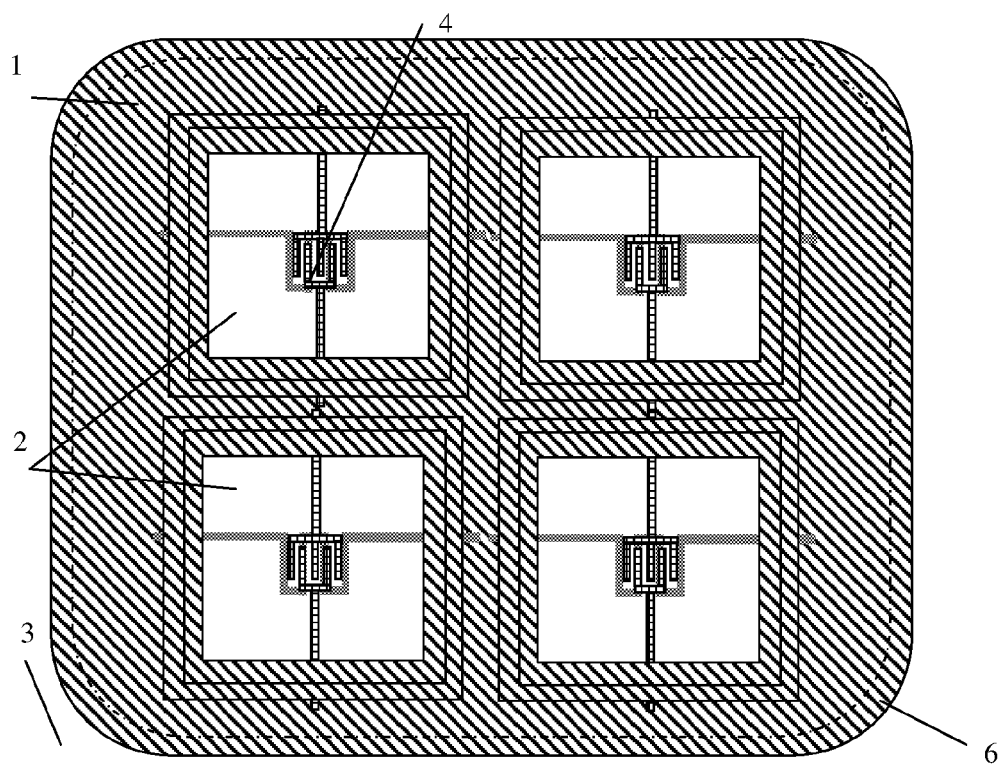
FIG. 22(c) shows a top view of an array of micro-heaters with rectangular rings 1 that extends over the membrane on a single membrane.

FIG. 22(*a*) shows a top view of a device with an array of micro-heaters 4 on a single membrane with a dummy ring 15 around each heater 4 and a ring 1 that overlaps the membrane 2 and the end of the etched silicon 6 to the silicon substrate 3.

FIG. 22(*b*) shows a top view of a device with an array of rings on a single membrane with a dummy ring 15 and a ring 1 that extends over the membrane 2 and overlaps the end of the etched silicon 6 to the silicon substrate 3. The membrane 2 may have any device, structures or none as may be desired.

FIG. 22(*c*) shows a top view of a an array of micro-heaters with rectangular rings 1 that extends over the membrane on a single membrane 2 that overlaps the end of the etched silicon 6 to the silicon substrate 3. The membrane 2 may have any device, structures or none as may be desired.

The embodiment of the ring 1 and the dummy ring 15 described in FIG. 22 can take any of the structures as described in FIG. 7 and FIG. 8.

Figure 23A:
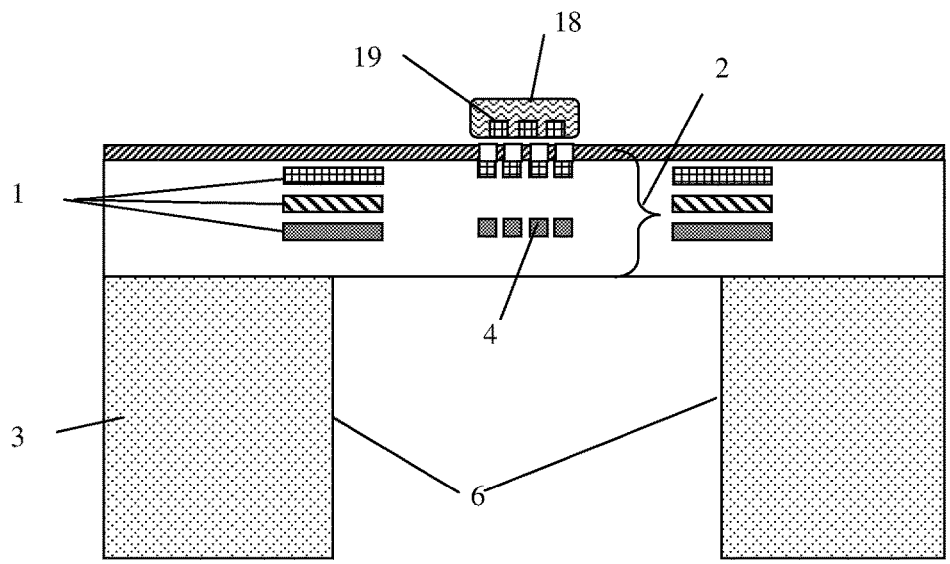
FIG. 23(a) shows the schematic cross-section of a micro-hotplate with a sensing material and post-CMOS process electrodes with a stack of ring layers on standard CMOS process.
Figure 23B:
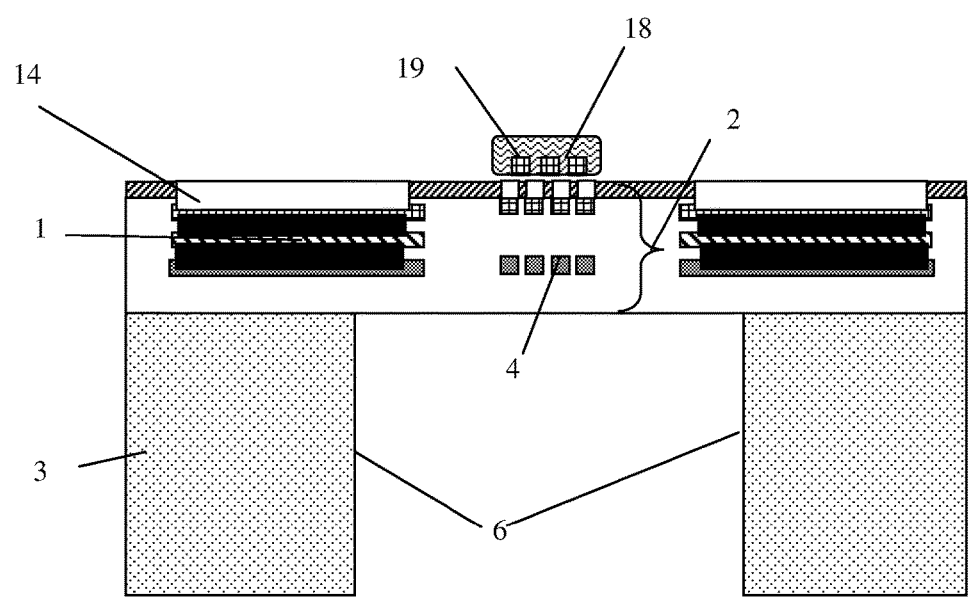
FIG. 23(b) shows an alternative schematic cross-section of a micro-hotplate with sensing material and post-CMOS process electrodes with a stack of ring layers on standard CMOS process.

FIG. 23(*a*) shows the schematic cross-section of a micro-hotplate with sensing material 18 and post-CMOS process electrodes 19 with a stack of ring 1 layers on standard CMOS process. The device illustrates the embodiment of the ring 1 with first, second and third metal layer, stacked vertically together with post-CMOS process layer that can be placed on the pad 14 or without the pad 14 that overlap membrane 2 and the end of the etched silicon 6 to the silicon substrate 3.

FIG. 23(*b*) shows the schematic cross-section of a micro-hotplate with sensing material 18 and post-CMOS process electrodes 19 with a stack of ring 1 layers on standard CMOS process. The device illustrates the embodiment of the ring 1 with first, second and third metal layer, stacked vertically together with post-CMOS process layer that can be placed on the pad 14 or without the pad 14. The embodiment of the ring can be contacted using inter-metal contacts as described in FIG. 8 using standard CMOS process that overlap membrane 2 and the end of the etched silicon 6 to the silicon substrate 3.

Figure 24A:
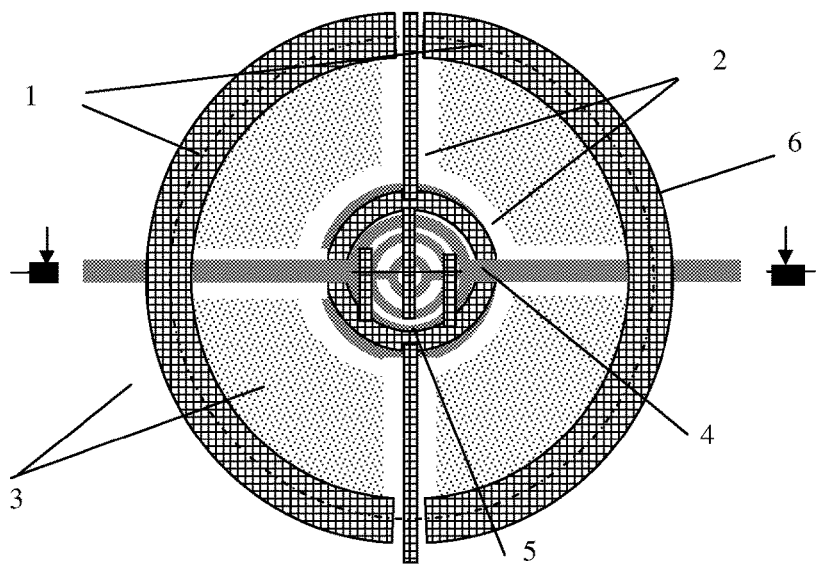
FIG. 24(a) shows a top view of a front-side etched micro-hotplate with electrodes supported by a suspended membrane and a ring layers that overlaps the membrane and substrate.
Figure 24B:
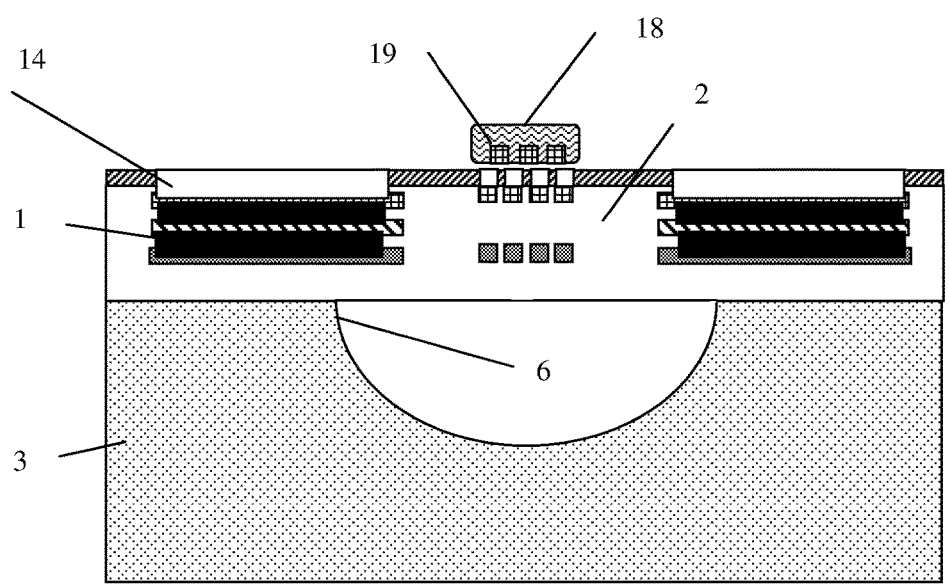
FIG. 24(b) shows a schematic cross-section of a front-side etched micro-hotplate with sensing material and post-CMOS process electrodes with a stack of ring layers on standard CMOS process.

FIG. 24(*a*) shows top view of a front-side etched micro-hotplate 4 with electrodes 5 supported by a suspended membrane 2 and a ring 1 layers that overlaps the membrane and substrate 3. The front-side etched membrane can be shapes and size where the ring can be added.

FIG. 24(*b*) shows the schematic cross-section of a front-side etched micro-hotplate with sensing material 18 and post-CMOS process electrodes 19 with a stack of ring 1 layers on standard CMOS process. The device illustrates the embodiment of the ring 1 with first, second and third metal layer, stacked vertically together with post-CMOS process layer that can be placed on the pad 14 or without the pad 14. The embodiment of the ring can be contacted using inter-metal contacts as described in FIG. 8 using standard CMOS process that overlap membrane 2 and the end of the etched silicon 6 to the silicon substrate 3.

Figure 25:
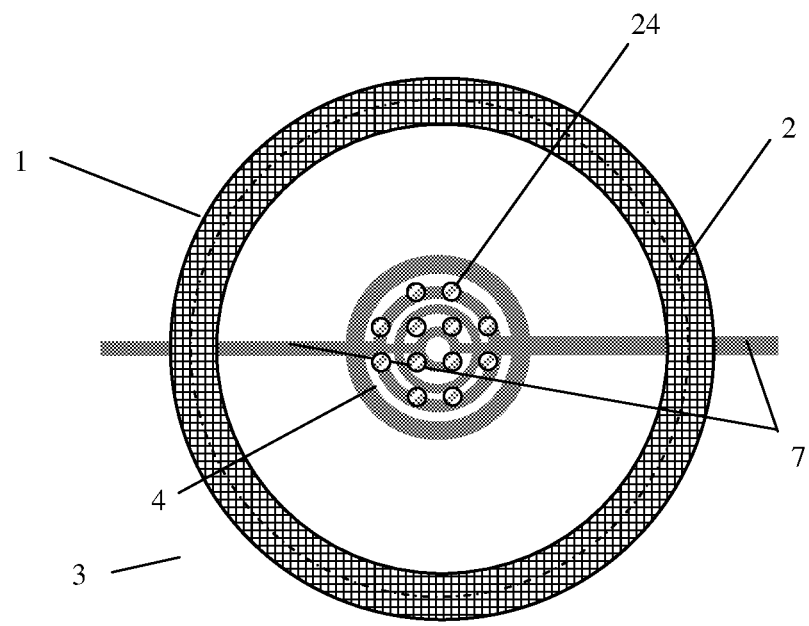
FIG. 25 shows top view of a micro-hotplate with plasmonic structures.

FIG. 25 shows top view of a micro-hotplate 4 with plasmonic structures (or the patterned layer) made with a metal layer or combinations of metal layers (or laterally spaced structures) 24 supported by a suspended membrane 2 and a ring 1 layers that overlaps the membrane and substrate 3. The plasmonic layer can be circular, holes and other shapes as appropriately needed for IR emission or absorption enhancements or response alterations. Such plasmonic layers can also be placed on IR detectors as shown in FIG. 21.

FIG. 26(*a*) shows top view of an embodiment with resistive temperature sensing ring 25 and temperature sensing diodes 27 and 28 placed on the membrane 2 between the perimeter of the micro-hotplate 4 and the ring 1 layers that overlaps the membrane and substrate 3. The diode 27 can be a single or multiple devices connected in series or in parallel by a metal track (or an interconnect layer) 26.

FIG. 26(*b*) the schematic cross-section of a micro-hotplate 4 with resistive temperature sensing ring 25 and temperature sensing diodes 27 and 28 placed on the membrane 2 between the perimeter of the micro-hotplate 4 and the ring 1 layers that overlaps the membrane and substrate 3. The embodiment of the device with resistive 25 and diode 27 or 28 temperature sensors can be similarly substituted with a thermopile or combination thereof. The device can have single or multiple temperature sensors located anywhere from the centre or the membrane to the edge of the ring or to the etched substrate 6.

FIG. 27 shows top view of an embodiment of a micro-hotplate 4 array with hexagonal ring 1 that overlaps the membrane 2, substrate 3 and edge of the etched substrate 6.

FIG. 28 illustrates an exemplary flow diagram outlining the manufacturing method of the micro-hotplate.

In summary, we disclose a micro-hotplate with a suspended heater located on a low thermal conductivity membrane (or the first portion of the dielectric region) in which a plate with high thermal conductivity in the form of a ring which extends partly above the substrate portion supporting the membrane and partly above or within the membrane is placed. The ring could be made in CMOS technology and may contain a metal layer such as Al, tungsten, titanium, copper or a combination of those. The ring could be provided by the same layer (using the same mask) as the heater. The ring could be made in CMOS technology and may contain a layer of silicon, polysilicon, silicide or a combination of those. The ring may be to provide a yield and performance increase to the membrane process. The over or under etching of the membrane could affect significantly the thermal performance (power consumption and thermal mass) and ultimately the yield of micro-hotplates in state-of-the-art devices. According to the embodiments of the invention the ring is fabricated in CMOS technology and is tightly aligned with only possible minor misalignment. The ring is designed to take some of the heat via conduction and improved convection and therefore the exact position of the membrane edge has a smaller effect on the thermal performance (power consumption and thermal mass) when compared to devices without a ring. According to this innovation, the presence of the ring will ensure better electro-thermal reproducibility (maximum and average temperature in micro-hotplates vs electrical power) from device to device within the same wafer at different locations, from wafer to wafer and from lot to lot. It has been demonstrated that the back etch (via dry—DRIE or wet techniques) could result in significant variation of the membrane size even within the same wafer from centre to edge. This variation could be as much as 10-20 um within the same wafer but could be more than 20 um from one wafer to another. Thus the ring is to provide a better mechanical stability preventing high deflections of the membrane and supporting mechanically the membrane to give (i) higher mechanical strength (ii) better reliability in long term operation. The ring is made of a continuous layer or the ring is made of a discontinuous layer with gaps between regions, to avoid for example any mechanical stress built in large areas of metals (during processing) but still provide increased thermal performance and mechanical robustness. There is more than one ring made in different layers (e.g. 2 or 3 metal layers or one metal layer and one poly layer). Temperature sensors such as diodes resistors or thermopiles could be placed within the membrane between the ring and the heater to give an accurate prediction of the temperature of the heater. This will be much more accurate for the micro-hotplates with rings as the temperature profile within the membrane could be more accurately predicted and is less affected by the exact location of the membrane etch. There is an optimisation of the extension of the ring inside the membrane, towards the heater, for a good trade-off between (i) power consumption, (ii) thermal transient response and (iii) electro-thermal reproducibility, mechanical strength and yield.

The skilled person will understand that in the preceding description and appended claims, positional terms such as 'above', 'below', 'front', 'back', 'vertical', 'underneath' etc. are made with reference to conceptual illustrations of a semiconductor device, such as those showing standard cross-sectional perspectives and those shown in the appended drawings. These terms are used for ease of reference but are not intended to be of limiting nature. These terms are therefore to be understood as referring to a semiconductor device when in an orientation as shown in the accompanying drawings.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein.

The invention claimed is:

1. A micro-hotplate comprising:
   a substrate comprising an etched portion and a substrate portion;
   a dielectric region over the substrate, wherein the dielectric region comprises first and second portions, wherein the first portion is adjacent to the etched portion of the substrate and the second portion is adjacent to the substrate portion of the substrate;
   a heater formed in the dielectric region; and
   a ring structure formed within or over the dielectric region such that the ring structure is coupled with the first and second portions of the dielectric region, wherein the ring structure is located along a perimeter of the first portion of the dielectric region, and wherein the ring structure is spaced from the heater by the dielectric region.

2. A micro-hotplate according to claim 1, wherein the first portion of the dielectric region is directly adjacent to the etched portion of the substrate and the second portion of the dielectric region is directly adjacent to the substrate portion of the substrate.

3. A micro-hotplate according to claim 1, wherein the ring structure is located such that the ring structure overlaps with the first and second portions of the dielectric region.

4. A micro-hotplate according to claim 1, wherein the ring structure is formed such that a portion of a width of the ring structure falls within the first portion of the dielectric region and a remaining portion of the width of the ring structure is located within the second portion of the dielectric region.

5. A micro-hotplate according to claim 1, wherein the ring structure is formed such that a portion of a width of the ring structure is located over the etched portion of the substrate and a remaining portion of the width of the ring structure is located over the substrate portion of the substrate.

6. A micro-hotplate according to claim 1, wherein the ring structure extends through an entire area of the second portion of the dielectric region so that the ring structure extends to a perimeter of an entire chip.

7. A micro-hotplate according to claim 1, wherein the ring structure comprises one or more ring layers.

8. A micro-hotplate according to claim 7, wherein:
   the ring structure comprises a first layer which is located at the same level as the heater within the dielectric region; or the ring structure comprises a second layer which is located at a higher level compared to the heater within the dielectric region; or the ring structure comprises a third layer which is located at a higher level compared to the heater within the dielectric region.

9. A micro-hotplate according to claim 7, wherein the ring structure comprises first, second and third layers stacked over one another within the dielectric region.

10. A micro-hotplate according to claim 7, wherein said one or more layers comprise a material selected from:
- a metal selected from aluminium, tungsten, titanium, copper and a combination of any of these materials; and
- polysilicon, single crystal silicon, a silicide and a combination of any of these materials.

11. A micro-hotplate according to claim 7, wherein said one or more ring layers are formed using CMOS or SOI-CMOS technique.

12. A micro-hotplate according to claim 7, wherein the ring structure comprises at least two metal layers stacked over one another within the dielectric region.

13. A micro-hotplate according to claim 12, further comprising an inter-metal contact between said at least two metal layers.

14. A micro-hotplate according to claim 13, wherein the inter-metal contact is located in the second portion of the dielectric region over the substrate portion of the substrate, and optionally the micro-hotplate comprises a further inter-metal contact which is located in the first portion of the dielectric region over the etched portion of the substrate.

15. A micro-hotplate according to claim 13, wherein the inter-metal contact extends in the first and second portions of the dielectric region over the etched and substrate portions of the substrate.

16. A micro-hotplate according to claim 1, further comprising an auxiliary ring structure between the heater and the ring structure, the auxiliary ring structure being located within the first portion of the dielectric region, and optionally the auxiliary ring structure and the ring structure being coupled using a plurality of support structures.

17. A micro-hotplate according to claim 1, wherein the ring structure has a circular or rectangular shape or any other shapes.

18. A micro-hotplate according to claim 1, further comprising an electrode layer over the first portion of the dielectric region and a sensing material over the electrode layer.

19. A micro-hotplate according to claim 18, wherein the micro-hotplate is an environmental sensing device.

20. A micro-hotplate according to claim 1, wherein the etched portion of the substrate is formed using an etching technique for back-etching the substrate, the etching technique being selected from a group comprising deep reactive ion etching (DRIE), anisotropic or crystallographic wet etching, potassium hydroxide (KOH) and tetramethyl ammonium hydroxide (TMAH).

21. A micro-hotplate according to claim 1, wherein the etched portion of the substrate is formed using a front etching technique.

22. A micro-hotplate according to claim 1, wherein the substrate is a semiconductor substrate.

23. A micro-hotplate according to claim 1, further comprising at least one patterned layer formed within or on the first portion of the dielectric region, wherein said at least one patterned layer comprises laterally spaced structures.

24. A micro-hotplate according to claim 23, wherein said at least one patterned layer is located over or under the heater.

25. A micro-hotplate according to claim 1, further comprising a plurality of heaters formed within the first portion of the dielectric region, and wherein optionally each heater is surrounded by an auxiliary ring structure formed within the first portion of the dielectric layer.

26. An array of micro-hotplates incorporating the micro-hotplate according to claim 1.

27. A semiconductor device comprising:
- a substrate comprising an etched portion and a substrate portion;
- a dielectric region over the substrate, wherein the dielectric region comprises first and second portions, wherein the first portion is adjacent to the etched portion of the substrate and the second portion is adjacent to the substrate portion of the substrate; and
- a ring structure formed within and/or over the dielectric region such that the ring structure is coupled with the first and second portions of the dielectric region, and wherein the ring structure is located along a perimeter of the first portion of the dielectric region, and wherein the ring structure is spaced from the heater by the dielectric region.

28. A semiconductor device according to claim 27, further comprising a heater within the first portion of the dielectric region, the heater being surrounded by the ring structure.

29. A semiconductor device according to claim 27, further comprising at least one temperature sensing device placed between centre of the first portion and the edge of the ring structure, wherein said at least one temperature sensing device comprises at least a partial ring shape.

30. A semiconductor device according to claim 29, further comprising a diode within the first portion of the dielectric region, the diode being connected in series or parallel with a interconnect layer.

31. A semiconductor device according to claim 27, further comprising a thermopile within the first portion of the dielectric region, the thermopile being surrounded by the ring structure.

32. A method of manufacturing a micro-hotplate, the method comprising:
- forming a substrate;
- depositing one or more layers of metals and/or dielectric layers to form a dielectric region;
- forming a heater in the dielectric region;
- forming a ring structure within or over the dielectric region;
- etching the substrate to form an etched portion of the substrate and a substrate portion of the substrate, wherein the etching of the substrate provides first and second portions in the dielectric region, wherein the first portion is adjacent to the etched portion of the substrate and the second portion is adjacent to the substrate portion of the substrate; and
- wherein the ring structure is formed such that the ring structure is coupled with the first and second portions of the dielectric region, and wherein the ring structure is located along a perimeter of the first portion of the dielectric region, and wherein the ring structure is spaced from the heater by the dielectric region.

* * * * *